United States Patent
Parihar

(10) Patent No.: US 10,058,310 B2
(45) Date of Patent: Aug. 28, 2018

(54) ELECTROSURGICAL DEVICE WITH DRUM-DRIVEN ARTICULATION

(71) Applicant: Ethicon Endo-Surgery, Inc., Cincinnati, OH (US)

(72) Inventor: Shailendra K. Parihar, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 805 days.

(21) Appl. No.: 13/798,551

(22) Filed: Mar. 13, 2013

(65) Prior Publication Data

US 2014/0276719 A1 Sep. 18, 2014

(51) Int. Cl.
| | | |
|---|---|---|
| *A61B 17/00* | (2006.01) | |
| *A61B 18/18* | (2006.01) | |
| *A61B 17/28* | (2006.01) | |
| *A61B 34/30* | (2016.01) | |
| *A61B 18/14* | (2006.01) | |

(52) U.S. Cl.
CPC ............ *A61B 17/00* (2013.01); *A61B 17/282* (2013.01); *A61B 18/18* (2013.01); *A61B 34/30* (2016.02); *A61B 18/1445* (2013.01); *A61B 2017/00477* (2013.01)

(58) Field of Classification Search
CPC . A61B 18/1445; A61B 19/2203; A61B 19/56; A61B 2019/2242; A61B 2019/2246; A61B 17/282; A61B 18/18; A61B 17/00; A61B 2017/00477; A61B 34/30
USPC .......................................................... 606/45
See application file for complete search history.

(56) References Cited

U.S. PATENT DOCUMENTS

| | | | |
|---|---|---|---|
| 2,715,341 A | 8/1955 | Hogan | |
| 2,818,744 A | 1/1958 | Moody | |
| 2,857,776 A | 10/1958 | Williams | |
| 2,881,645 A | 4/1959 | Kruchten | |
| 3,194,530 A | 7/1965 | Heyl | |
| 4,203,430 A | 5/1980 | Takahashi | |
| 4,483,562 A | 11/1984 | Schoolman | |
| 4,723,936 A | 2/1988 | Buchbinder et al. | |

(Continued)

FOREIGN PATENT DOCUMENTS

| | | |
|---|---|---|
| DE | 43 00 307 | 7/1994 |
| FR | 2 915 873 | 11/2008 |

(Continued)

OTHER PUBLICATIONS

U.S. Appl. No. 13/443,101, filed Apr. 10, 2012, Martin et al.

(Continued)

*Primary Examiner* — Christopher D Koharski
*Assistant Examiner* — Pamela M Bays
(74) *Attorney, Agent, or Firm* — Frost Brown Todd LLC

(57) ABSTRACT

A surgical device for operating on tissue comprises an end effector, a shaft, and an interface assembly. The shaft comprises an articulation section operable to provide deflection of the end effector relative to the longitudinal axis of the shaft. The interface assembly comprises a plurality of pulleys associated with drive shafts driven by an external system. The pulleys are operable to cause rotation of one or both of the shaft or end effector. The pulleys are further operable to cause articulation of the articulation section. The interface assembly further comprises drive components operable to cause movement of components of the end effector.

18 Claims, 23 Drawing Sheets

(56) References Cited

U.S. PATENT DOCUMENTS

| | | | |
|---|---|---|---|
| 4,880,015 | A | 11/1989 | Nierman |
| 4,945,920 | A | 8/1990 | Clossick |
| 5,020,514 | A | 6/1991 | Heckele |
| 5,125,895 | A | 6/1992 | Buchbinder et al. |
| 5,330,502 | A | 7/1994 | Hassler et al. |
| 5,383,888 | A | 1/1995 | Zvenyatsky et al. |
| 5,391,180 | A | 2/1995 | Tovey et al. |
| 5,395,329 | A | 3/1995 | Fleischhacker et al. |
| 5,411,519 | A | 5/1995 | Tovey et al. |
| 5,441,499 | A | 8/1995 | Fritzsch |
| 5,454,827 | A | 10/1995 | Aust et al. |
| 5,462,546 | A | 10/1995 | Rydell |
| 5,514,130 | A | 5/1996 | Baker |
| 5,514,157 | A | 5/1996 | Nicholas et al. |
| 5,540,685 | A | 7/1996 | Parins et al. |
| 5,549,637 | A | 8/1996 | Crainich |
| 5,562,682 | A | 10/1996 | Oberlin et al. |
| 5,607,450 | A | 3/1997 | Zvenyatsky et al. |
| 5,609,601 | A | 3/1997 | Kolesa et al. |
| 5,632,432 | A | 5/1997 | Schulze et al. |
| 5,643,294 | A | 7/1997 | Tovey et al. |
| 5,700,275 | A | 12/1997 | Bell et al. |
| 5,743,456 | A | 4/1998 | Jones et al. |
| 5,766,196 | A | 6/1998 | Griffiths |
| 5,766,205 | A | 6/1998 | Zvenyatsky et al. |
| 5,782,859 | A | 7/1998 | Nicholas et al. |
| 5,792,135 | A | 8/1998 | Madhani et al. |
| 5,817,084 | A | 10/1998 | Jensen |
| 5,878,193 | A | 3/1999 | Wang et al. |
| 5,921,956 | A | 7/1999 | Grinberg et al. |
| 5,931,832 | A | 8/1999 | Jensen |
| 6,162,208 | A | 12/2000 | Hipps |
| 6,179,809 | B1 | 1/2001 | Khairkhahan et al. |
| 6,231,565 | B1 | 5/2001 | Tovey et al. |
| 6,364,888 | B1 | 4/2002 | Niemeyer et al. |
| 6,423,059 | B1 | 7/2002 | Hanson et al. |
| 6,500,176 | B1 | 12/2002 | Truckai et al. |
| 6,554,794 | B1 | 4/2003 | Mueller et al. |
| RE38,335 | E | 11/2003 | Aust et al. |
| 6,783,524 | B2 | 8/2004 | Anderson et al. |
| 6,991,627 | B2 | 1/2006 | Madhani et al. |
| 7,004,938 | B2 | 2/2006 | Ormsby et al. |
| 7,070,595 | B2 | 7/2006 | Ormsby et al. |
| 7,081,114 | B2 | 7/2006 | Rashidi |
| 7,087,071 | B2 | 8/2006 | Nicholas et al. |
| 7,112,201 | B2 | 9/2006 | Truckai et al. |
| 7,125,409 | B2 | 10/2006 | Truckai et al. |
| 7,141,897 | B2 | 11/2006 | Park |
| 7,150,749 | B2 | 12/2006 | Dycus et al. |
| 7,156,846 | B2 | 1/2007 | Dycus et al. |
| 7,159,750 | B2 | 1/2007 | Racenet et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,208,005 | B2 | 4/2007 | Frecker et al. |
| 7,220,951 | B2 | 5/2007 | Truckai et al. |
| 7,309,849 | B2 | 12/2007 | Truckai et al. |
| 7,311,709 | B2 | 12/2007 | Truckai et al. |
| 7,331,967 | B2 | 2/2008 | Lee et al. |
| 7,354,440 | B2 | 4/2008 | Truckai et al. |
| 7,380,696 | B2 | 6/2008 | Shelton, IV et al. |
| 7,381,209 | B2 | 6/2008 | Truckai et al. |
| 7,404,508 | B2 | 7/2008 | Smith et al. |
| 7,407,076 | B2 | 8/2008 | Racenet et al. |
| 7,424,965 | B2 | 9/2008 | Racenet et al. |
| 7,455,208 | B2 | 11/2008 | Wales et al. |
| 7,464,849 | B2 | 12/2008 | Shelton, IV et al. |
| 7,481,348 | B2 | 1/2009 | Marczyk |
| 7,494,039 | B2 | 2/2009 | Racenet et al. |
| 7,506,790 | B2 | 3/2009 | Shelton, IV |
| 7,524,320 | B2 | 4/2009 | Tierney et al. |
| 7,540,872 | B2 | 6/2009 | Schechter et al. |
| 7,549,564 | B2 | 6/2009 | Boudreaux |
| 7,553,275 | B2 | 6/2009 | Padget et al. |
| 7,559,450 | B2 | 7/2009 | Wales et al. |
| 7,584,880 | B2 | 9/2009 | Racenet et al. |
| 7,594,913 | B2 | 9/2009 | Ormsby et al. |
| 7,597,230 | B2 | 10/2009 | Racenet et al. |
| 7,615,044 | B2 | 11/2009 | Scheibe et al. |
| 7,654,431 | B2 | 2/2010 | Hueil et al. |
| 7,691,095 | B2 | 4/2010 | Bednarek et al. |
| 7,691,098 | B2 | 4/2010 | Wallace et al. |
| 7,703,653 | B2 | 4/2010 | Shah et al. |
| 7,708,182 | B2 | 5/2010 | Viola |
| 7,721,935 | B2 | 5/2010 | Racenet et al. |
| 7,771,425 | B2 | 8/2010 | Dycus et al. |
| 7,780,054 | B2 | 8/2010 | Wales |
| 7,784,662 | B2 | 8/2010 | Wales et al. |
| 7,793,814 | B2 | 9/2010 | Racenet et al. |
| 7,798,386 | B2 | 9/2010 | Schall et al. |
| 7,799,028 | B2 | 9/2010 | Schechter et al. |
| 7,806,891 | B2 | 10/2010 | Nowlin et al. |
| 7,815,090 | B2 | 10/2010 | Marczyk |
| 7,815,091 | B2 | 10/2010 | Marczyk |
| 7,815,637 | B2 | 10/2010 | Ormsby et al. |
| 7,824,401 | B2 | 11/2010 | Manzo et al. |
| 7,828,725 | B2 | 11/2010 | Maruyama |
| 7,909,220 | B2 | 3/2011 | Viola |
| 8,006,365 | B2 | 8/2011 | Levin et al. |
| 8,033,441 | B2 | 10/2011 | Marczyk |
| 8,062,306 | B2 | 11/2011 | Nobis et al. |
| 8,092,451 | B2 | 1/2012 | Schechter et al. |
| 8,100,309 | B2 | 1/2012 | Marczyk |
| 8,142,473 | B2 | 3/2012 | Cunningham |
| 8,152,799 | B2 | 4/2012 | Ormsby et al. |
| 8,161,838 | B2 | 4/2012 | Duval |
| 8,197,479 | B2 | 6/2012 | Olson et al. |
| 8,205,619 | B2 | 6/2012 | Shah et al. |
| 8,236,010 | B2 | 8/2012 | Ortiz et al. |
| 8,241,320 | B2 | 8/2012 | Lyons et al. |
| 8,292,147 | B2 | 10/2012 | Viola |
| 8,292,889 | B2 | 10/2012 | Cunningham et al. |
| 8,317,811 | B2 | 11/2012 | Laporte Rosello et al. |
| 8,323,239 | B2 | 12/2012 | Bednarek et al. |
| 8,323,297 | B2 | 12/2012 | Hinman et al. |
| 8,353,902 | B2 | 1/2013 | Prakash |
| 8,357,161 | B2 | 1/2013 | Mueller |
| 8,361,067 | B2 | 1/2013 | Pellegrino et al. |
| 8,366,709 | B2 | 2/2013 | Schechter et al. |
| 8,372,064 | B2 | 2/2013 | Douglass et al. |
| 8,403,832 | B2 | 3/2013 | Cunningham et al. |
| 8,700,213 | B2 | 4/2014 | Kawashima et al. |
| 9,089,360 | B2 | 7/2015 | Messerly et al. |
| 2006/0079874 | A1 | 4/2006 | Faller et al. |
| 2006/0259071 | A1 | 11/2006 | Nicholas et al. |
| 2007/0043353 | A1 | 2/2007 | Dycus et al. |
| 2007/0191713 | A1 | 8/2007 | Eichmann et al. |
| 2007/0219550 | A1 | 9/2007 | Thompson et al. |
| 2007/0282324 | A1 | 12/2007 | Vaska et al. |
| 2007/0282333 | A1 | 12/2007 | Fortson et al. |
| 2008/0161798 | A1 | 7/2008 | Podmore et al. |
| 2008/0200940 | A1 | 8/2008 | Eichmann et al. |
| 2009/0088774 | A1* | 4/2009 | Swarup ............... A61B 19/2203 606/130 |
| 2009/0125019 | A1 | 5/2009 | Douglass et al. |
| 2009/0283568 | A1 | 11/2009 | Racenet et al. |
| 2010/0094289 | A1 | 4/2010 | Taylor et al. |
| 2010/0179540 | A1 | 7/2010 | Marczyk et al. |
| 2010/0179545 | A1 | 7/2010 | Twomey et al. |
| 2010/0249759 | A1 | 9/2010 | Hinman et al. |
| 2010/0298824 | A1 | 11/2010 | Rothstein et al. |
| 2011/0009863 | A1 | 1/2011 | Marczyk et al. |
| 2011/0015660 | A1 | 1/2011 | Wiener et al. |
| 2011/0028486 | A1 | 2/2011 | Dinnell et al. |
| 2011/0087212 | A1 | 4/2011 | Aldridge et al. |
| 2011/0087213 | A1 | 4/2011 | Messerly et al. |
| 2011/0087214 | A1 | 4/2011 | Giordano et al. |
| 2011/0087215 | A1 | 4/2011 | Aldridge et al. |
| 2011/0087216 | A1 | 4/2011 | Aldridge et al. |
| 2011/0087217 | A1 | 4/2011 | Yates et al. |
| 2011/0087218 | A1 | 4/2011 | Boudreaux et al. |
| 2011/0184459 | A1 | 7/2011 | Malkowski et al. |
| 2011/0213360 | A1 | 9/2011 | Cunningham et al. |
| 2011/0213361 | A1 | 9/2011 | Cunningham et al. |

(56) References Cited

U.S. PATENT DOCUMENTS

| | | |
|---|---|---|
| 2011/0213363 A1 | 9/2011 | Cunningham et al. |
| 2011/0230875 A1 | 9/2011 | Walberg et al. |
| 2011/0264074 A1 | 10/2011 | Tegg et al. |
| 2011/0282176 A1 | 11/2011 | Tegg |
| 2011/0288573 A1* | 11/2011 | Yates ............... A61B 17/07207 606/170 |
| 2012/0078243 A1* | 3/2012 | Worrell ............ A61B 17/07207 606/33 |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0109186 A1 | 5/2012 | Parrott et al. |
| 2012/0116379 A1 | 5/2012 | Yates et al. |
| 2012/0132450 A1 | 5/2012 | Timm et al. |
| 2012/0138660 A1 | 6/2012 | Shelton, IV |
| 2012/0143088 A1 | 6/2012 | Schultz |
| 2012/0179151 A1 | 7/2012 | Mueller |
| 2012/0199630 A1 | 8/2012 | Shelton, IV |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203169 A1 | 8/2012 | Tegg |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |
| 2012/0215220 A1 | 8/2012 | Kerver et al. |
| 2012/0253326 A1 | 10/2012 | Kleyman |
| 2012/0265186 A1 | 10/2012 | Burger et al. |
| 2012/0298719 A1* | 11/2012 | Shelton, IV ..... A61B 17/07207 227/176.1 |
| 2012/0303013 A1 | 11/2012 | Hauck et al. |
| 2012/0316560 A1 | 12/2012 | Hassoun |
| 2013/0012929 A1 | 1/2013 | Malkowski |
| 2013/0012957 A1 | 1/2013 | Shelton, IV et al. |
| 2013/0012986 A1 | 1/2013 | Suzuki |
| 2013/0023868 A1* | 1/2013 | Worrell ............ A61B 17/07207 606/33 |
| 2013/0030428 A1 | 1/2013 | Worrell et al. |
| 2013/0032627 A1 | 2/2013 | Viola |
| 2013/0041403 A1 | 2/2013 | Cunningham et al. |
| 2013/0096407 A1 | 4/2013 | Bednarek et al. |

FOREIGN PATENT DOCUMENTS

| | | |
|---|---|---|
| WO | WO 00/67834 | 11/2000 |
| WO | WO 2012/067468 | 5/2012 |
| WO | WO 2012/078951 | 6/2012 |

OTHER PUBLICATIONS

U.S. Appl. No. 61/550,768, filed Oct. 24, 2011, Monson.
U.S. Appl. No. 61/597,603, filed Feb. 10, 2012, Parihar et al.
Abstract and Machine Translation of German Patent No. DE 43 00 307.
Abstract and Machine Translation of French Patent No. FR 2 915 873.
International Search Report and Written Opinion dated Jun. 10, 2014 for Application No. PCT/US2014/016844, 10 pgs.

* cited by examiner

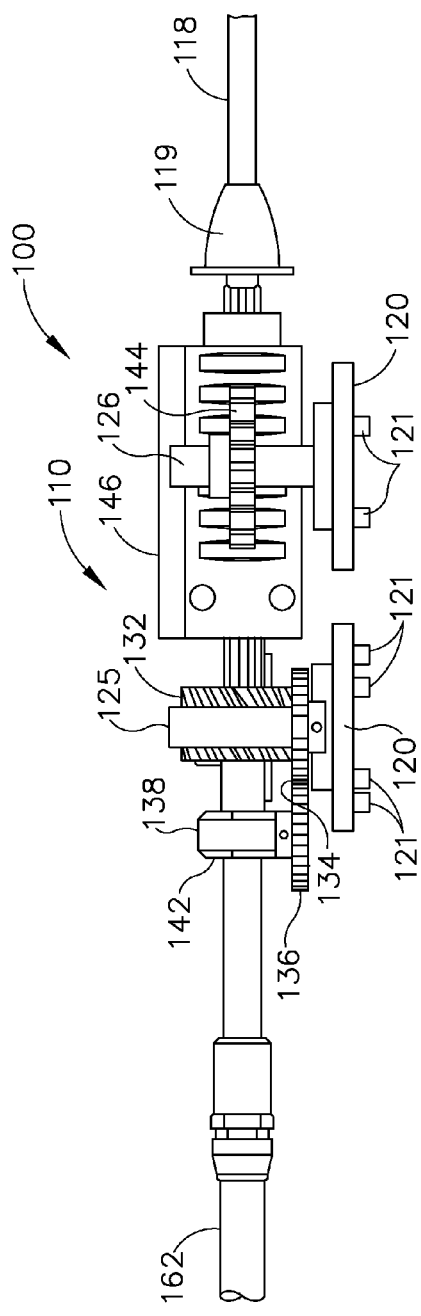
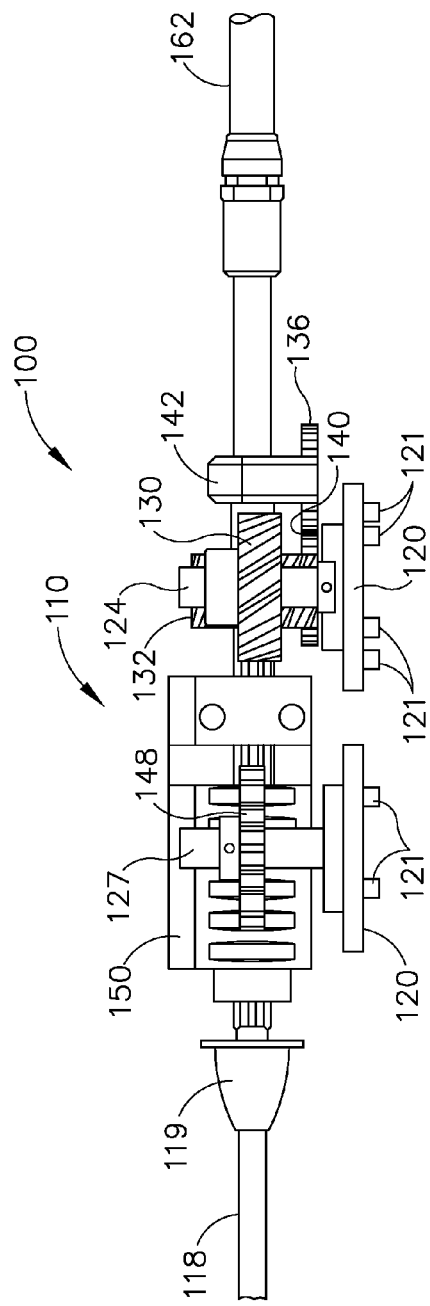
Fig. 12
Fig. 13

ELECTROSURGICAL DEVICE WITH DRUM-DRIVEN ARTICULATION

BACKGROUND

A variety of surgical instruments include a tissue cutting element and one or more elements that transmit radio frequency (RF) energy to tissue (e.g., to coagulate or seal the tissue). An example of an RF electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein; U.S. Pub. No. 2012/0078243, entitled "Control Features for Articulating Surgical Device," published Mar. 29, 2012, now U.S. Pat. No. 9,877,720, issued Jan. 30, 2018, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, issued Aug. 2, 2016, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,327, issued Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, now U.S. Pat. No. 9,545,253, issued Jan. 17, 2017, the disclosure of which is incorporated by reference herein.

In addition, a variety of surgical instruments include a shaft having an articulation section, providing enhanced positioning capabilities for an end effector that is located distal to the articulation section of the shaft. Examples of such devices include various models of the ENDOPATH® endocutters by Ethicon Endo-Surgery, Inc., of Cincinnati, Ohio. Further examples of such devices and related concepts are disclosed in U.S. Pat. No. 7,380,696, entitled "Articulating Surgical Stapling Instrument Incorporating a Two-Piece E-Beam Firing Mechanism," issued Jun. 3, 2008, the disclosure of which is incorporated by reference herein; U.S. Pat. No. 7,404,508, entitled "Surgical Stapling and Cutting Device," issued Jul. 29, 2008, the disclosure of which is incorporated by reference herein; U.S. Pat. No. 7,455,208, entitled "Surgical Instrument with Articulating Shaft with Rigid Firing Bar Supports," issued Nov. 25, 2008, the disclosure of which is incorporated by reference herein; U.S. Pat. No. 7,506,790, entitled "Surgical Instrument Incorporating an Electrically Actuated Articulation Mechanism," issued Mar. 24, 2009, the disclosure of which is incorporated by reference herein; U.S. Pat. No. 7,549,564, entitled "Surgical Stapling Instrument with an Articulating End Effector," issued Jun. 23, 2009, the disclosure of which is incorporated by reference herein; U.S. Pat. No. 7,559,450, entitled "Surgical Instrument Incorporating a Fluid Transfer Controlled Articulation Mechanism," issued Jul. 14, 2009, the disclosure of which is incorporated by reference herein; U.S. Pat. No. 7,654,431, entitled "Surgical Instrument with Guided Laterally Moving Articulation Member," issued Feb. 2, 2010, the disclosure of which is incorporated by reference herein; U.S. Pat. No. 7,780,054, entitled "Surgical Instrument with Laterally Moved Shaft Actuator Coupled to Pivoting Articulation Joint," issued Aug. 24, 2010, the disclosure of which is incorporated by reference herein; U.S. Pat. No. 7,784,662, entitled "Surgical Instrument with Articulating Shaft with Single Pivot Closure and Double Pivot Frame Ground," issued Aug. 31, 2010, the disclosure of which is incorporated by reference herein; and U.S. Pat. No. 7,798,386, entitled "Surgical Instrument Articulation Joint Cover," issued Sep. 21, 2010, the disclosure of which is incorporated by reference herein.

Some surgical systems provide robotic control of a surgical instrument. With minimally invasive robotic surgery, surgical operations may be performed through a small incision in the patient's body. A robotic surgical system may be used with various types of surgical instruments, including but not limited to surgical staplers, ultrasonic instruments, electrosurgical instruments, and/or various other kinds of instruments, as will be described in greater detail below. An example of a robotic surgical system is the DAVINCI™ system by Intuitive Surgical, Inc., of Sunnyvale, Calif. By way of further example, one or more aspects of robotic surgical systems are disclosed in the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No.

6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; and U.S. Pat. No. 7,824,401, entitled "Surgical Tool With Writed Monopolar Electrosurgical End Effectors," issued Nov. 2, 2010, the disclosure of which is incorporated by reference herein.

Additional examples of instruments that may be incorporated with a robotic surgical system are described in U.S. Pub. No. 2013/0012957, entitled "Automated End Effector Component Reloading System for Use with a Robotic System, published Jan. 10, 2013, now U.S. Pat. No. 8,844,789, issued Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, now U.S. Pat. No. 8,820,605, issued Sep. 2, 2014, the disclosure of which is incorporated by reference herein; U.S. Pub. No. 2012/0132450, entitled "Shiftable Drive Interface for Robotically-Controlled Surgical Tool," published May 31, 2012, now U.S. Pat. No. 8,616,431, issued Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, now U.S. Pat. No. 8,573,461, issued Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, now U.S. Pat. No. 8,602,288, issued Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued Apr. 5, 2016, the disclosure of which is incorporated by reference herein; U.S. Pub. No. 2012/0203247, entitled "Robotically-Controlled Surgical End Effector System," published Aug. 9, 2012, now U.S. Pat. No. 8,783,541, issued Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, now U.S. Pat. No. 8,479,969, issued Jul. 9, 2014; U.S. Pub. No. 2012/0138660, entitled "Robotically-Controlled Cable-Based Surgical End Effectors," published Jun. 7, 2012, now U.S. Pat. No. 8,800,838, issued Aug. 12, 2014, the disclosure of which is incorporated by reference herein; U.S. Pub. No. 2012/0205421, entitled "Robotically-Controlled Surgical End Effector System with Rotary Actuated Closure Systems," published Aug. 16, 2012, the disclosure of which is incorporated by reference herein; U.S. Pat. No. 9,814,457, entitled "Control Interface for Laparoscopic Suturing Instrument," issued Nov. 4, 2017, the disclosure of which is incorporated by reference herein; and U.S. Provisional Pat. App. No. 61/597,603, entitled "Robotically Controlled Surgical Instrument," filed Feb. 10, 2012, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 12 depicts a left side elevational view of the surgical instrument of FIG. 4, with the top cover removed;

FIG. 13 depicts a right side elevational view of the surgical instrument of FIG. 4, with the top cover removed;

Figure 1:
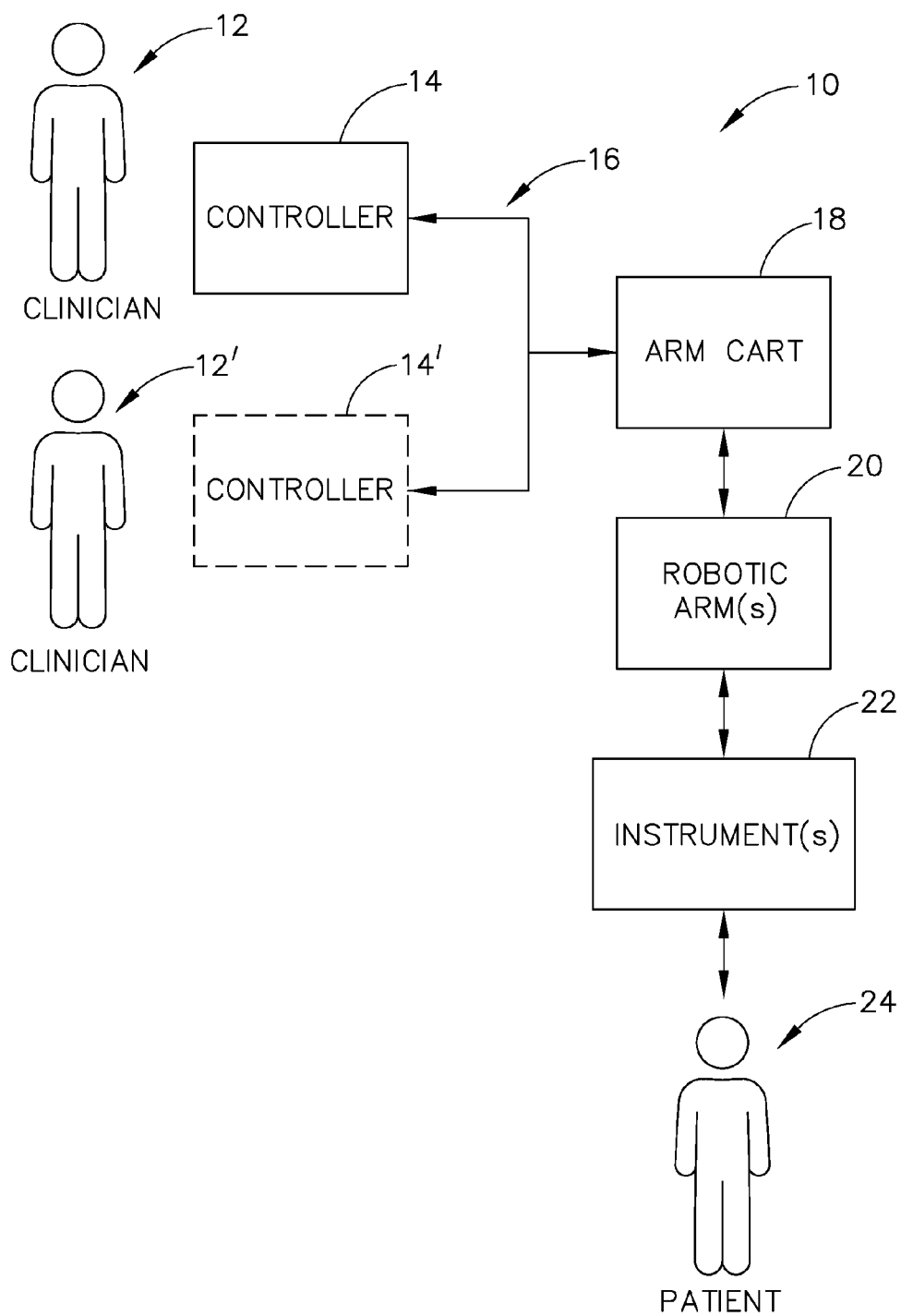
FIG. 1 depicts a block diagram of an exemplary robotic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a robotic surgical driver comprising a proximal housing having an interface that mechanically and electrically couples with a surgical instrument having a distal surgical end effector. The term "proximal" refers the position of an element closer to the robotic surgical driver housing and the term "distal" refers to the position of an element closer to the surgical end effector of the surgical instrument and further away from the housing.

I. Exemplary Robotic Surgical System Overview

FIG. 1 illustrates an exemplary robotic surgical system (10). System (10) comprises at least one controller (14) and at least one arm cart (18). Arm cart (18) is mechanically and/or electrically coupled to one or more robotic manipulators or arms (20). Each robotic arm (20) comprises one or more surgical instruments (22) for performing various surgical tasks on a patient (24). Operation of arm cart (18), including arms (20) and instruments (22), may be directed by a clinician (12) from controller (14). In some examples, a second controller (14'), operated by a second clinician (12'), may also direct operation of the arm cart (18) in conjunction with the first clinician (12'). For example, each of the clinicians (12, 12') may control different arms (20) of the cart or, in some cases, complete control of arm cart (18) may be passed between the clinicians (12, 12'). In some examples, additional arm carts (not shown) may be utilized on the patient (24). These additional arm carts may be controlled by one or more of the controllers (14, 14').

Arm cart(s) (18) and controllers (14, 14') may be in communication with one another via a communications link (16), which may be any suitable type of wired and/or wireless communications link carrying any suitable type of signal (e.g., electrical, optical, infrared, etc.) according to any suitable communications protocol. Communications link (16) may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network.

Figure 2:
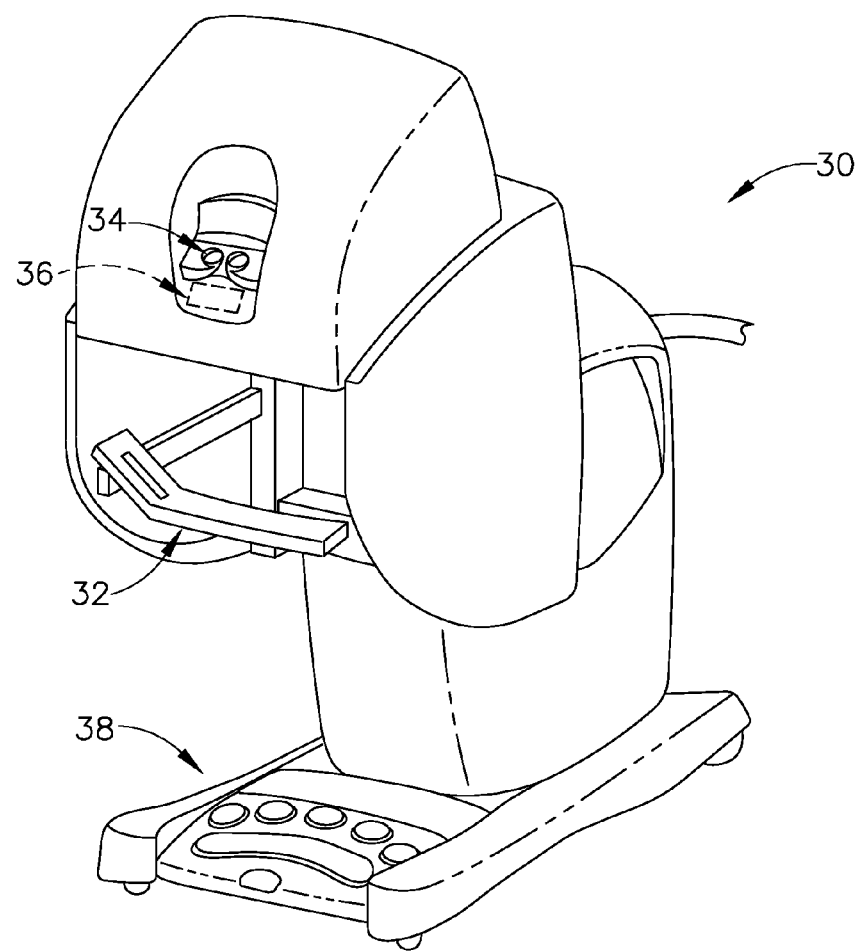
FIG. 2 depicts a perspective view of an exemplary controller of the system of FIG. 1.

FIG. 2 shows an exemplary controller (30) that may serve as a controller (14) of system (10). In this example, controller (30) generally includes user input assembly (32) having precision user input features (not shown) that are grasped by the surgeon and manipulated in space while the surgeon views the surgical procedure via a stereo display (34). The user input features of user input assembly (32) may include manual input devices that move with multiple degrees of freedom; and that include an actuatable handle for intuitively actuating tools (e.g., for closing grasping saws, applying an electrical potential to an electrode, etc). Controller (30) of the present example also includes an array of footswitches (38) providing additional control of arms (20) and instruments (22) to the surgeon. Display (34) may show views from one or more endoscopes viewing the surgical site within the patient and/or any other suitable view(s). In addition, a feedback meter (36) may be viewed through the display (34) and provide the surgeon with a visual indication of the amount of force being applied to a component of instrument (22) (e.g., a cutting member or clamping member, etc.). Other sensor arrangements may be employed to provide controller (30) with an indication as to whether a staple cartridge (or some other device) has been loaded into an end effector of instrument (22), whether an anvil of instrument (22) has been moved to a closed position prior to firing, and/or some other operational condition of instrument (22).

Figure 3:
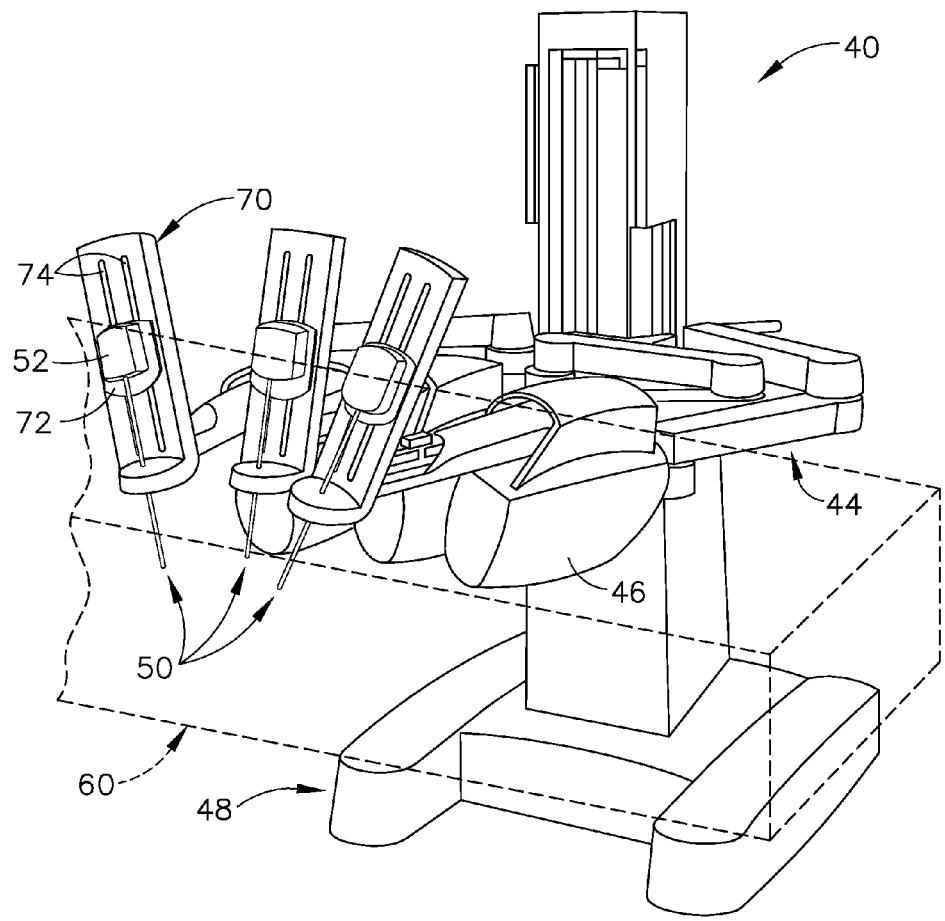
FIG. 3 depicts a perspective view of an exemplary robotic arm cart of the system of FIG. 1.
Figure 4:
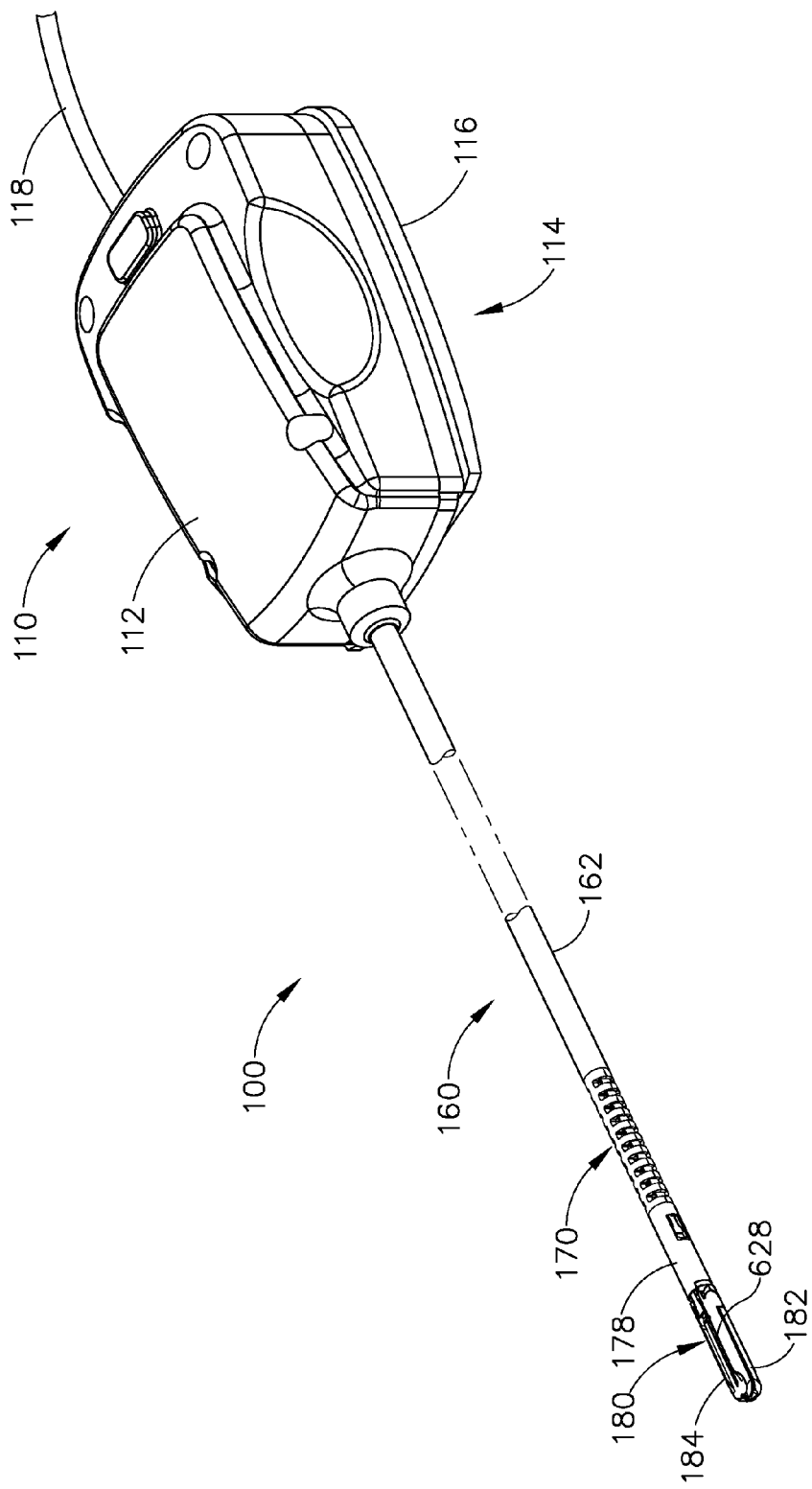
FIG. 4 depicts a perspective view of an exemplary surgical instrument suitable for incorporation with the system of FIG. 1.

FIG. 3 shows an exemplary robotic arm cart (40) that may serve as of arm cart (18) of system (10). In this example, arm cart (40) is operable to actuate a plurality of surgical instruments (50). While three instruments (50) are shown in this example, it should be understood that arm cart (40) may be operable to support and actuate any suitable number of surgical instruments (50). Surgical instruments (50) are each supported by a series of manually articulatable linkages, generally referred to as set-up joints (44), and a robotic manipulator (46). These structures are herein illustrated with protective covers extending over much of the robotic linkage. These protective covers may be optional, and may be limited in size or entirely eliminated in some versions to minimize the inertia that is encountered by the servo mechanisms used to manipulate such devices, to limit the volume of moving components so as to avoid collisions, and to limit the overall weight of cart (40).

Each robotic manipulator (46) terminates at an instrument platform (70), which is pivotable, rotatable, and otherwise movable by manipulator (46). Each platform includes an instrument dock (72) that is slidable along a pair of tracks (74) to further position instrument (50). Such sliding is motorized in the present example. Each instrument dock (72) includes mechanical and electrical interfaces that couple with an interface assembly (52) of instrument (50). By way of example only, dock (72) may include four rotary outputs that couple with complementary rotary inputs of interface assembly (52). Such rotary drive features may drive various functionalities in instrument (50), such as is described in various references cited herein and/or as is described in greater detail below. Electrical interfaces may establish communication via physical contact, inductive coupling, and/or otherwise; and may be operable to provide electrical power to one or more features in instrument (50), provide commands and/or data communication to instrument (50), and/or provide commands and/or data communication from instrument (50). Various suitable ways in which an instrument dock (72) may mechanically and electrically communicate with an interface assembly (52) of an instrument (50) will be apparent to those of ordinary skill in the art in view of the teachings herein. It should also be understood that instrument (50) may include one or more cables that couple with a separate power source and/or control unit, to provide communication of power and/or commands/data to/from instrument (50).

Arm cart (40) of the present example also includes a base (48) that is movable (e.g., by a single attendant) to selectively position arm cart (40) in relation to a patient. Cart (40) may generally have dimensions suitable for transporting the cart (40) between operating rooms. Cart (40) may be configured to fit through standard operating room doors and onto standard hospital elevators. In some versions, an automated instrument reloading system (not shown) may also be positioned in or near the work envelope (60) of arm cart (40), to selectively reload components (e.g., staple cartridges, etc.) of instruments (50).

In addition to the foregoing, it should be understood that one or more aspects of system (10) may be constructed in accordance with at least some of the teachings of U.S. Pat. No. 5,792,135; U.S. Pat. No. 5,817,084; U.S. Pat. No. 5,878,193; U.S. Pat. No. 6,231,565; U.S. Pat. No. 6,783,524; U.S. Pat. No. 6,364,888; U.S. Pat. No. 7,524,320; U.S. Pat. No. 7,691,098; U.S. Pat. No. 7,806,891; U.S. Pat. No. 7,824,401; and/or U.S. Pub. No. 2013/0012957, now U.S. Pat. No. 8,844,789, issued Sep. 30, 2014. The disclosures of each of the foregoing U.S. Patents and U.S. Patent Publication are incorporated by reference herein. Still other suitable features and operabilities that may be incorporated into system (10) will be apparent to those of ordinary skill in the art in view of the teachings herein.

II. Exemplary Electrosurgical Instrument with Articulation Feature

FIGS. 4-13 show an exemplary electrosurgical instrument (100) that may be used as at least one instrument (50) within system (10). At least part of instrument (100) may be constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, now U.S. Pat. No. 8,939,974, issued Jan. 27, 2015; U.S. Pub. No. 2012/0116379, now U.S. Pat. No. 9,161,803, issued Oct. 20, 2015; U.S. Pub. No. 2012/0078243, now U.S. Pat. No. 9,877,720, issued Jan. 30, 2018; U.S. Pub. No. 2012/0078247, now U.S. Pat. No. 9,402,682, issued Aug. 2, 2016; U.S. Pub. No. 2013/0030428, now U.S. Pat. No. 9,089,327, issued Jul. 28, 2015; and/or U.S. Pub. No. 2013/0023868, now U.S. Pat. No. 9,545,253, issued Jan. 17, 2017. As described therein and as will be described in greater detail below, instrument (100) is operable to cut tissue and seal or weld tissue (e.g., a blood vessel, etc.) substantially simultaneously. In other words, instrument (100) operates similar to an endocutter type of stapler, except that instrument (100) provides tissue welding through application of bipolar RF energy instead of providing lines of staples to join tissue. It should also be understood that instrument (100) may have various structural and functional similarities with the ENSEAL® Tissue Sealing Device by Ethicon Endo-Surgery, Inc., of Cincinnati, Ohio. Furthermore, instrument (100) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to instrument (100), there is no intent for any of the description herein to be presumed as admitted prior art. Several teachings herein will in fact go beyond the scope of the teachings of the references cited herein and the ENSEAL® Tissue Sealing Device by Ethicon Endo-Surgery, Inc., of Cincinnati, Ohio.

Instrument (100) of the present example includes an interface assembly (110), a shaft assembly (160), an articulation section (170), and an end effector (180). Interface assembly (110) is configured to couple with a dock (72) of robotic arm cart (40) and is thereby further operable to drive articulation section (170) and end effector (180) as will be described in greater detail below. As will also be described in greater detail below, instrument (100) is operable to articulate end effector (180) to provide a desired positioning relative to tissue (e.g., a large blood vessel, etc.), then sever the tissue and apply bipolar RF energy to the tissue with end effector (180) to thereby seal the tissue.

A. Exemplary Shaft Assembly and Articulation Section

Figure 5:
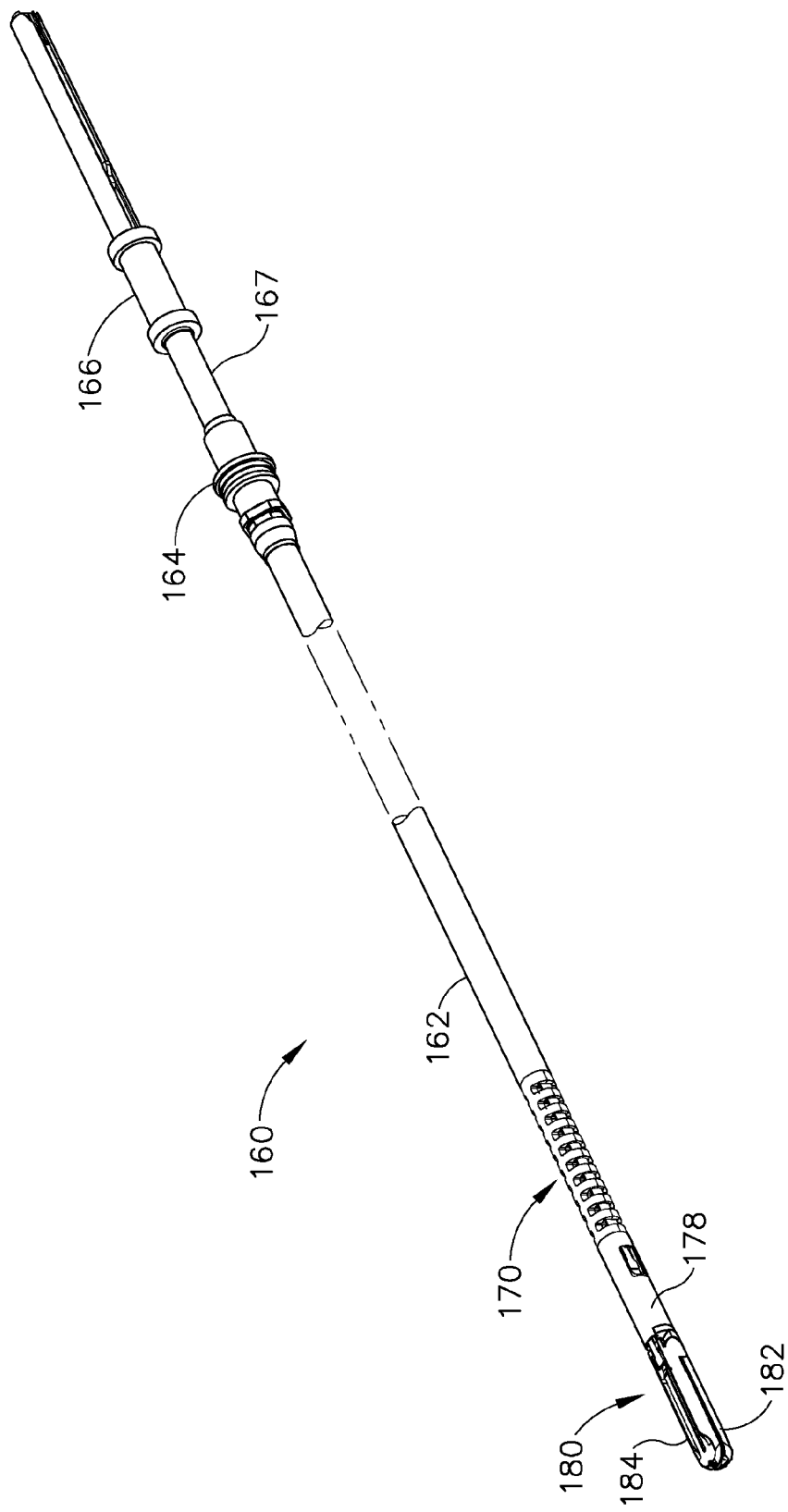
FIG. 5 depicts a perspective view of the shaft assembly of the surgical instrument of FIG. 4.

Shaft assembly (160) of the present example extends distally from interface assembly (110). Articulation section (170) is located at the distal end of shaft assembly (160), with end effector (180) being located distal to articulation section (170). Shaft assembly (160) includes an outer sheath (162) that encloses drive features and electrical features that couple interface assembly (110) with articulation section (170) and end effector (180). As best seen in FIG. 5, shaft assembly (160) further includes a unitary rotary coupling (164) and a firing beam coupling (166). Shaft assembly (160) is rotatable about the longitudinal axis defined by sheath (162), relative to interface assembly (110), via rotary coupling (164). Such rotation may provide rotation of end effector (180), articulation section (170), and shaft assembly (160) unitarily. In some other versions, rotary coupling (164) is operable to rotate end effector (180) without rotating any portion of shaft assembly (160) that is proximal of articulation section (170). As another merely illustrative example, instrument (100) may include one rotation control that provides rotatability of shaft assembly (160) and end effector (180) as a single unit; and another rotation control that provides rotatability of end effector (180) without rotating any portion of shaft assembly (160) that is proximal of articulation section (170). Other suitable rotation schemes will be apparent to those of ordinary skill in the art in view of the teachings herein. Of course, rotatable features may simply be omitted if desired.

Articulation section (170) is operable to selectively position end effector (180) at various angles relative to the longitudinal axis defined by sheath (162). Articulation section (170) may take a variety of forms. By way of example only, articulation section (170) may be configured in accordance with one or more teachings of U.S. Pub. No. 2012/0078247, now U.S. Pat. No. 9,402,682, issued Aug. 2, 2016, the disclosure of which is incorporated by reference herein. As another merely illustrative example, articulation section (170) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued Dec. 29, 2015, the disclosure of which is incorporated by reference herein. Various other suitable forms that articulation section (170) may take will be apparent to those of ordinary skill in the art in view of the teachings herein. It should also be understood that some versions of instrument (10) may simply lack articulation section (170).

Figure 6:
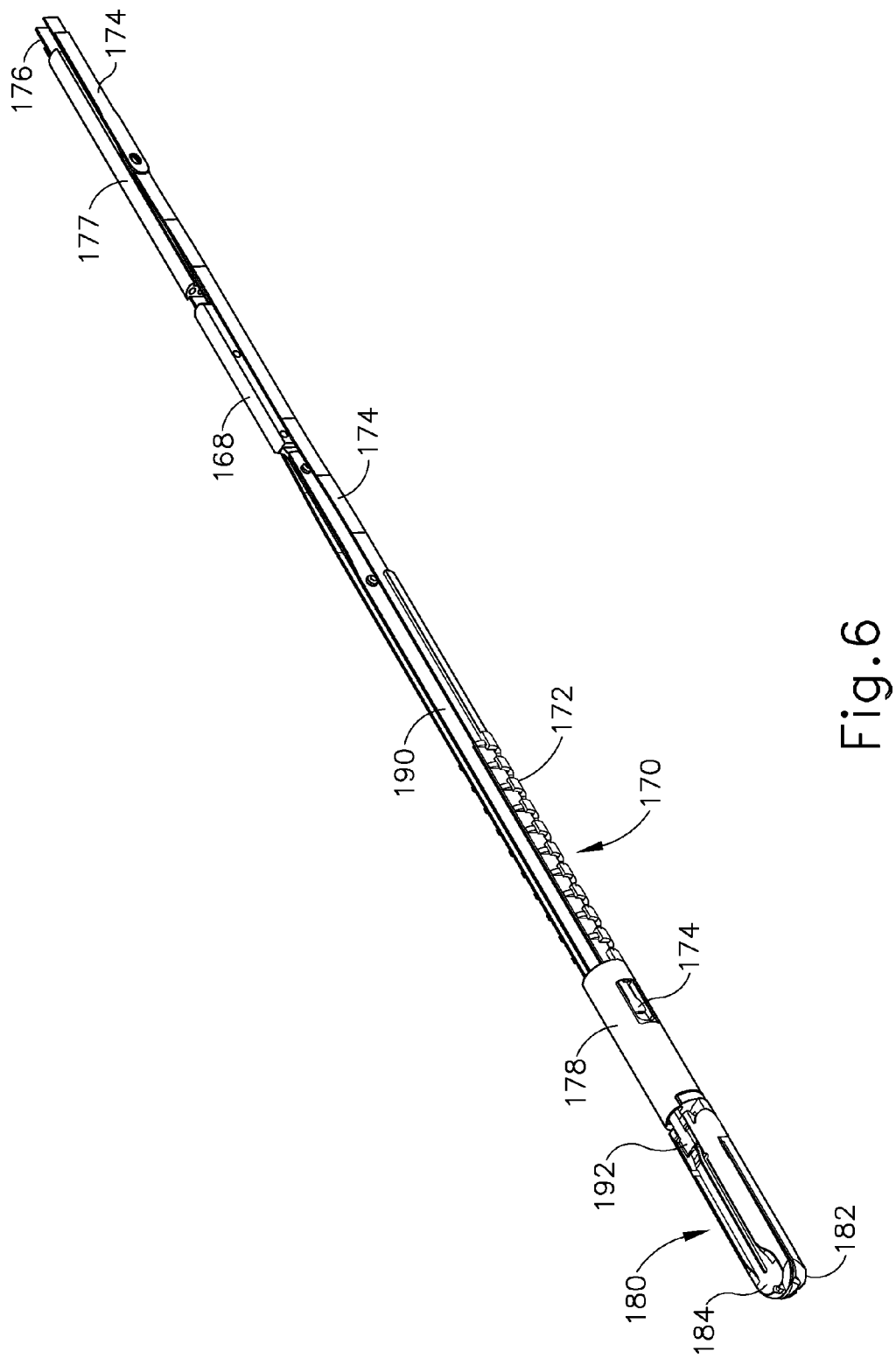
FIG. 6 depicts a perspective view of components of the shaft assembly of FIG. 5.
Figure 7:
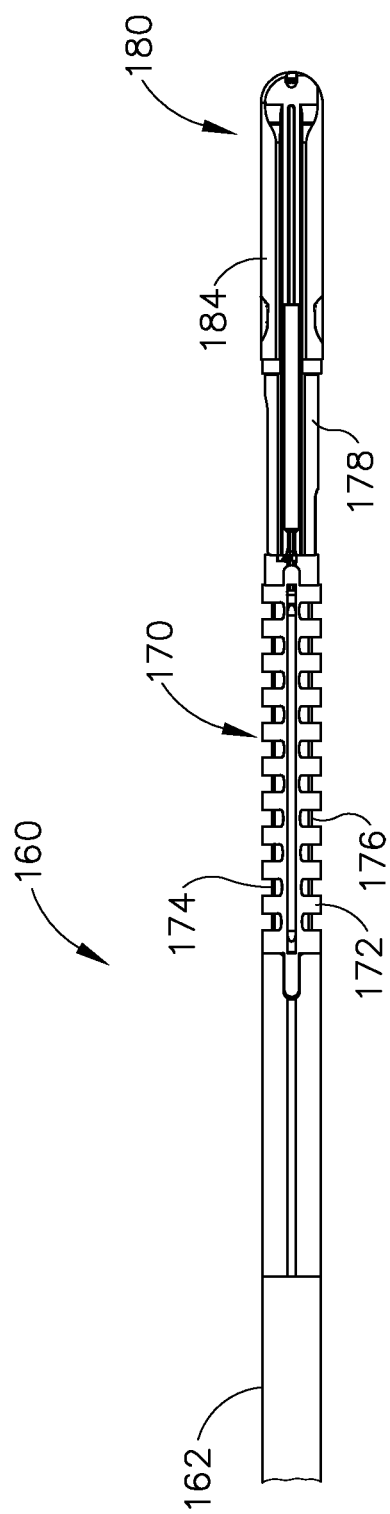
FIG. 7 depicts a top plan view of a distal portion of the shaft assembly of FIG. 5.

As best seen in FIGS. 6-7, articulation section (170) of the present example comprises a ribbed body (172) with a pair of articulation beams (174, 176) extending through ribbed body (172). An upper half of ribbed body (172) is omitted in FIG. 6. Articulation beams (174, 176) are distally anchored within a tube (178) that is positioned between end effector (180) and articulation section (170). Articulation beams (174, 176) are operable to articulate end effector (180) by laterally deflecting end effector (180) away from the longitudinal axis defined by sheath (162). In particular, and referring to the view shown in FIG. 7, end effector (180) will deflect toward articulation beam (174) when articulation beam (174) is retracted proximally while articulation beam (176) is advanced distally. End effector (180) will deflect toward articulation beam (176) when articulation beam (176) is retracted proximally while articulation beam (174) is advanced distally. Merely illustrative examples of how articulation beams (174, 176) may be opposingly translated will be described in greater detail below, while still other examples will be apparent to those of ordinary skill in the art in view of the teachings herein. As best seen in FIG. 6, a spacer body (177) is positioned between articulation beams (174, 176) and is operable to maintain beams (174, 176) in a substantially straight, separated relationship.

B. Exemplary End Effector

End effector (180) of the present example comprises a first jaw (182) and a second jaw (184). In the present example, first jaw (182) is substantially fixed relative to shaft assembly (160); while second jaw (184) pivots relative to shaft assembly (160), toward and away from first jaw (182). In some versions, actuators such as rods or cables, etc., may extend through sheath (162) and be joined with second jaw (184) at a pivotal coupling, such that longitudinal movement of the actuator rods/cables/etc. through shaft assembly (160) provides pivoting of second jaw (184) relative to shaft assembly (160) and relative to first jaw (182). Of course, jaws (182, 184) may instead have any other suitable kind of movement and may be actuated in any other suitable fashion. By way of example only, and as will be described in greater detail below, jaws (182, 184) may be actuated and thus closed by longitudinal translation of a firing beam (190), such that actuator rods/cables/etc. may simply be eliminated in some versions.

Figure 8:
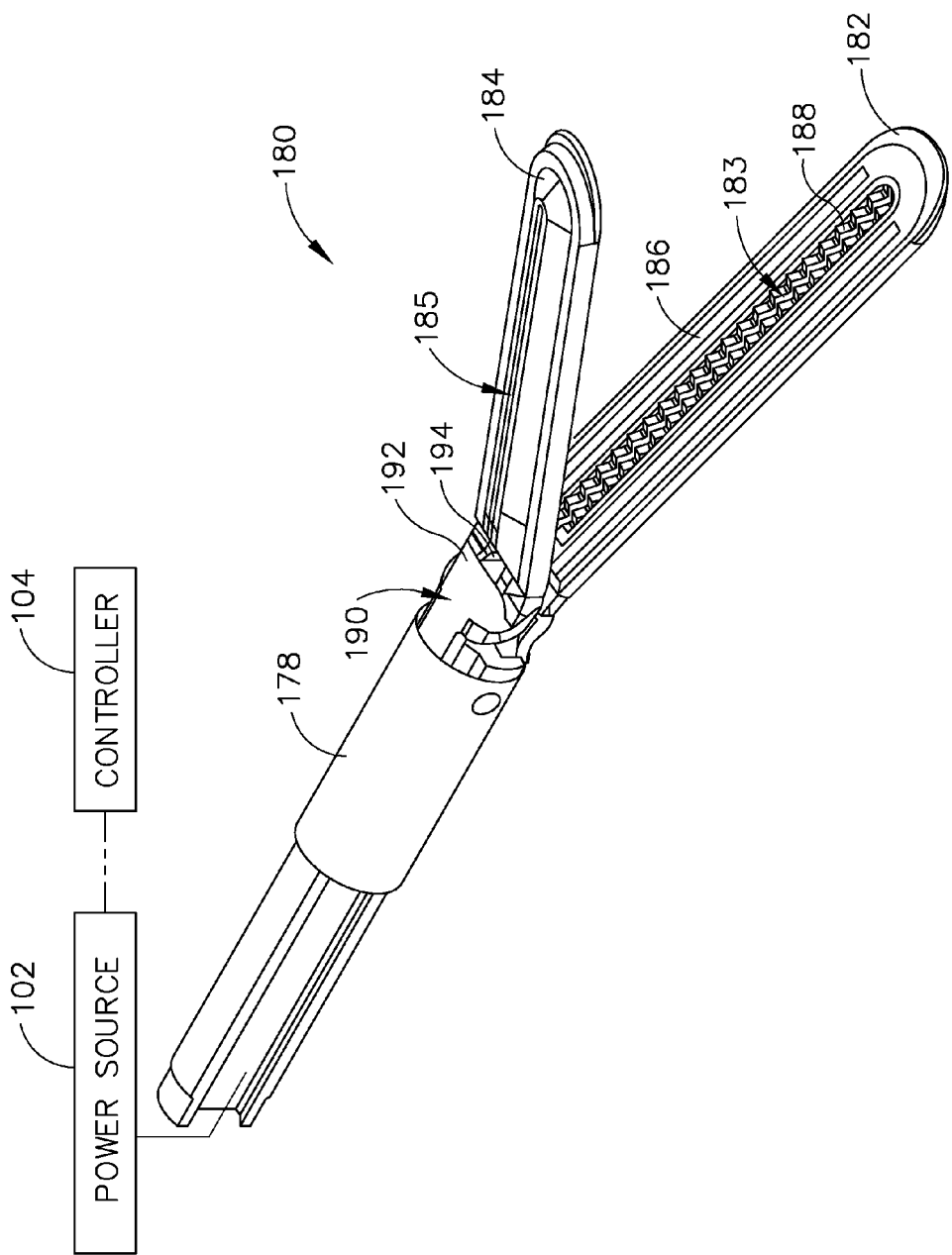
FIG. 8 depicts a perspective view of the end effector of the shaft assembly of FIG. 5, in an open configuration.
Figure 9:
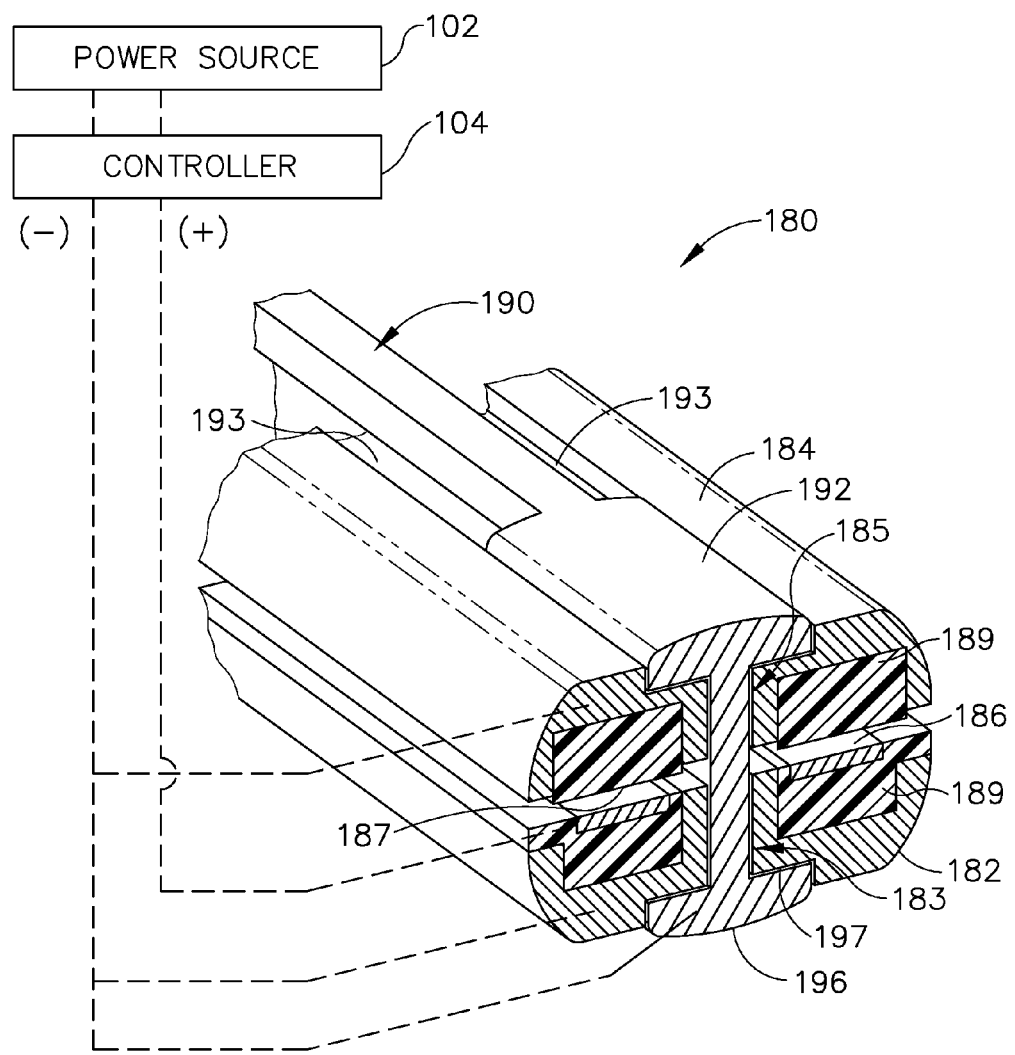
FIG. 9 depicts a perspective view in cross-section of the end effector of FIG. 8, taken along a lateral plane, with the end effector in a closed configuration.

As best seen in FIGS. 8-9, first jaw (182) defines a longitudinally extending elongate slot (183); while second jaw (184) also defines a longitudinally extending elongate slot (185). In addition, the top side of first jaw (182) presents a first electrode surface (186); while the underside of second jaw (184) presents a second electrode surface (187). Electrode surface (186, 187) are in communication with an electrical source (102) via one or more conductors (not shown) that extend along the length of shaft assembly (160). Electrical source (102) is operable to deliver RF energy to first electrode surface (186) at a first polarity and to second electrode surface (187) at a second (opposite) polarity, such that RF current flows between electrode surface (186, 187) and thereby through tissue captured between jaws (182, 184). In some versions, firing beam (190) serves as an electrical conductor that cooperates with electrode surface (186, 187) (e.g., as a ground return) for delivery of bipolar RF energy captured between jaws (182, 184).

Electrical source (102) may be external to instrument (100) or may be integral with instrument (100), as described in one or more references cited herein or otherwise. A controller (104) regulates delivery of power from electrical source (102) to electrode surfaces (186, 187). Controller (104) may also be external to instrument (100) or may be integral with electrosurgical instrument (100), as described in one or more references cited herein or otherwise. It should also be understood that electrode surfaces (186, 187) may be provided in a variety of alternative locations, configurations, and relationships. It should also be understood that power source (102) and/or controller (104) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, now U.S. Pat. No. 8,951,248, issued Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, now U.S. Pat. No. 9,039,695, issued May 26, 2015, the disclosure of which is incorporated by reference herein; U.S. Pub. No. 2011/0087215, entitled "Surgical Generator for Ultrasonic and Electrosurgical Devices," published Apr. 14, 2011, now U.S. Pat. No. 9,050,093, issued Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, now U.S. Pat. No. 8,956,349, issued Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, now U.S. Pat. No. 9,060,776, issued Jun. 23, 2015, the disclosure of which is incorporated by reference herein. Other suitable configurations for power source (102) and controller (104) will be apparent to those of ordinary skill in the art in view of the teachings herein.

As best seen in FIG. 9, the lower side of first jaw (182) includes a longitudinally extending recess (197) adjacent to slot (183); while the upper side of second jaw (184) includes a longitudinally extending recess (193) adjacent to slot (185). FIG. 2 shows the upper side of first jaw (182) including a plurality of teeth serrations (188). It should be understood that the lower side of second jaw (184) may include complementary serrations that nest with serrations (188), to enhance gripping of tissue captured between jaws (182, 184) without necessarily tearing the tissue. Of course, serrations (188) may take any other suitable form or may be simply omitted altogether. It should also be understood that serrations (188) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (182, 184).

With jaws (182, 184) in a closed position, shaft assembly (160) and end effector (180) are sized and configured to fit through trocars having various inner diameters, such that instrument (100) is usable in minimally invasive surgery, though of course instrument (100) could also be used in open procedures if desired. By way of example only, with jaws (182, 184) in a closed position, shaft assembly (160) and end effector (180) may present an outer diameter of approximately 5 mm. Alternatively, shaft assembly (160) and end effector (180) may present any other suitable outer diameter (e.g., between approximately 2 mm and approximately 20 mm, etc.).

In some versions, end effector (180) includes one or more sensors (not shown) that are configured to sense a variety of parameters at end effector (180), including but not limited to temperature of adjacent tissue, electrical resistance or impedance of adjacent tissue, voltage across adjacent tissue, forces exerted on jaws (182, 184) by adjacent tissue, etc. By way of example only, end effector (180) may include one or more positive temperature coefficient (PTC) thermistor bodies (189) (e.g., PTC polymer, etc.), located adjacent to electrodes (186, 187) and/or elsewhere. Data from sensors may be communicated to controller (104). Controller (104) may process such data in a variety of ways. By way of example only, controller (104) may modulate or otherwise change the RF energy being delivered to electrode surface (186, 187), based at least in part on data acquired from one or more sensors at end effector (180). In addition or in the alternative, controller (104) may alert the user to one or more conditions via an audio and/or visual feedback device (e.g., speaker, lights, display screen, etc.), based at least in part on data acquired from one or more sensors at end effector (180). It should also be understood that some kinds of sensors need not necessarily be in communication with controller (104), and may simply provide a purely localized effect at end effector (180). For instance, PTC thermistor bodies (189) at end effector (180) may automatically reduce the energy delivery at electrode surface (186, 187) as the temperature of the tissue and/or end effector (180) increases, thereby reducing the likelihood of overheating. In some such versions, a PTC thermistor element is in series with power source (102) and electrode surface (186, 187); and the PTC thermistor provides an increased impedance (reducing flow of current) in response to temperatures exceeding a threshold. Furthermore, it should be understood that electrode surface (186, 187) may be used as sensors (e.g., to sense tissue impedance, etc.). Various kinds of sensors that may be incorporated into instrument (100) will be apparent to those of ordinary skill in the art in view of the teachings herein. Similarly various things that can be done with data from sensors, by controller (104) or otherwise, will be apparent to those of ordinary skill in the art in view of the teachings herein. Other suitable variations for end effector (180) will also be apparent to those of ordinary skill in the art in view of the teachings herein.

Firing beam (190) is longitudinally movable along part of the length of end effector (180). Firing beam (190) is coaxially positioned within shaft assembly (160), extends along part of the length of shaft assembly (160), and translates longitudinally within shaft assembly (160) (including articulation section (170) in the present example), though it should be understood that firing beam (190) and shaft assembly (160) may have any other suitable relationship. As shown in FIG. 6, firing beam (190) is secured to a firing block (168), such that firing beam (190) and firing block (168) translate unitarily together within sheath (162). Firing block (168) is secured to firing tube (167), which is best seen in FIG. 5. Firing block (168) and firing tube (167) translate unitarily together within sheath (162). Firing beam coupling (166) is secured to firing tube (167), such that translating firing beam coupling (166) will translate firing beam (190) through the above-described couplings.

Firing beam (190) includes a sharp distal blade (194), an upper flange (192), and a lower flange (196). As best seen in FIGS. 8-9, distal blade (194) extends through slots (183, 185) of jaws (182, 184), with upper flange (192) being located above jaw (184) in recess (59) and lower flange (196) being located below jaw (182) in recess (58). The configuration of distal blade (194) and flanges (62, 66) provides an "I-beam" type of cross section at the distal end of firing beam (190). While flanges (192, 196) extend longitudinally only along a small portion of the length of firing beam (190) in the present example, it should be understood that flanges (192, 196) may extend longitudinally along any suitable length of firing beam (190). In addition, while flanges (192, 196) are positioned along the exterior of jaws (182, 184), flanges (192, 196) may alternatively be disposed in corresponding slots formed within jaws (182, 184). For instance, each jaw (182, 184) may define a "T"-shaped slot, with parts of distal blade (194) being disposed in one vertical portion of each "T"-shaped slot and with flanges (192, 196) being disposed in the horizontal portions of the "T"-shaped slots. Various other suitable configurations and relationships will be apparent to those of ordinary skill in the art in view of the teachings herein.

Distal blade (194) is substantially sharp, such that distal blade (194) will readily sever tissue that is captured between jaws (182, 184). Distal blade (194) is also electrically grounded in the present example, providing a return path for RF energy as described elsewhere herein. In some other versions, distal blade (194) serves as an active electrode. In addition or in the alternative, distal blade (194) may be selectively energized with ultrasonic energy (e.g., harmonic vibrations at approximately 55.5 kHz, etc.).

The "I-beam" type of configuration of firing beam (190) provides closure of jaws (182, 184) as firing beam (190) is advanced distally. In particular, flange (192) urges jaw (184) pivotally toward jaw (182) as firing beam (190) is advanced from a proximal position to a distal position, by bearing against recess (193) formed in jaw (184). This closing effect on jaws (182, 184) by firing beam (190) may occur before distal blade (194) reaches tissue captured between jaws (182, 184). Such staging of encounters by firing beam (190) may reduce the force required to actuate firing beam (190) distally through a full firing stroke. In other words, in some such versions, firing beam (190) may have already overcome an initial resistance required to substantially close jaws (182, 184) on tissue before encountering resistance from severing the tissue captured between jaws (182, 184). Of course, any other suitable staging may be provided.

In the present example, flange (192) is configured to cam against a ramp feature at the proximal end of jaw (184) to open jaw (184) when firing beam (190) is retracted to a proximal position and to hold jaw (184) open when firing beam (190) remains at the proximal position. This camming capability may facilitate use of end effector (180) to separate layers of tissue, to perform blunt dissections, etc., by forcing jaws (182, 184) apart from a closed position. In some other versions, jaws (182, 184) are resiliently biased to an open position by a spring or other type of resilient feature. While jaws (182, 184) close or open as firing beam (190) is translated in the present example, it should be understood that other versions may provide independent movement of jaws (182, 184) and firing beam (190). By way of example only, one or more cables, rods, beams, or other features may extend through shaft assembly (160) to selectively actuate jaws (182, 184) independently of firing beam (190).

C. Exemplary Robotic Arm Interface Assembly

FIGS. 4 and 10-13 show interface assembly (110) of the present example in greater detail. As shown, interface assembly (110) comprises a housing (112), a base (114), and a cable (118). Housing (112) comprises a shell that simply encloses drive components. In some versions, housing (112) also includes an electronic circuit board, chip, and/or other feature that is configured to identify instrument (100). Such identification may be carried out through cable (118). Cable (118) is configured to couple with power source (102) and controller (104). A strain relief (119) is provided at the interface of cable (118) and housing (112). It should be noted that housing (112) is omitted from FIGS. 11-13 for the sake of clarity.

Figure 10:
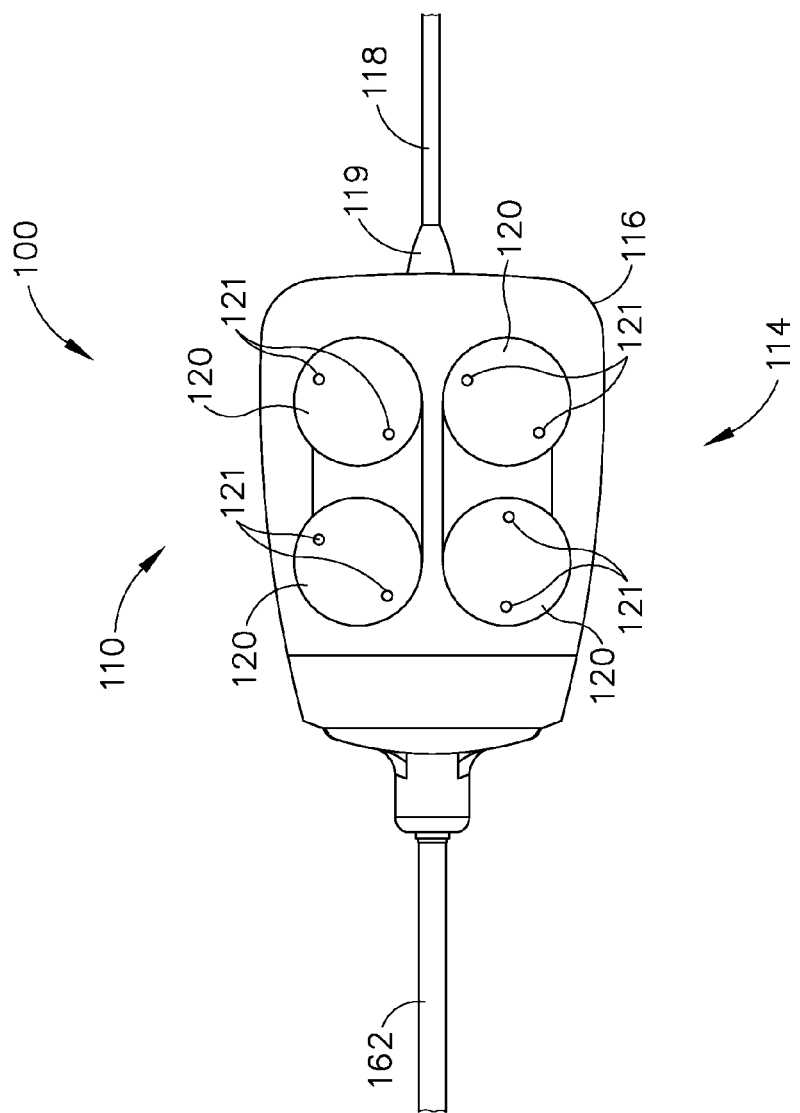
FIG. 10 depicts a bottom plan view of a proximal portion of the surgical instrument of FIG. 4.
Figure 11:
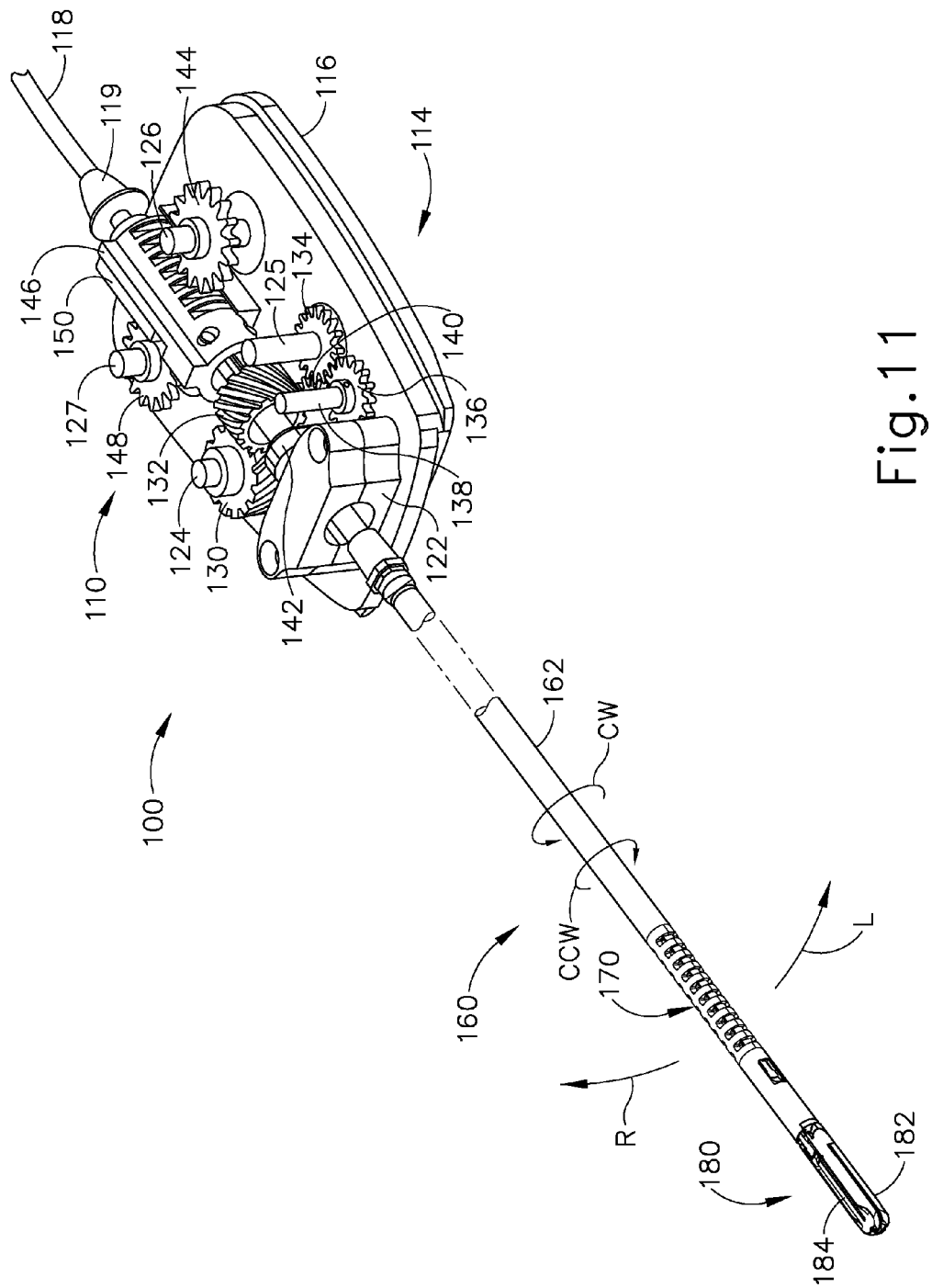
FIG. 11 depicts a perspective view of the surgical instrument of FIG. 4, with a top cover removed.

Base (114) includes a mounting plate (116) that engages dock (72) of robotic arm cart (40). It should be noted that plate (116) is omitted from FIGS. 12-13 for the sake of clarity. While not shown, it should be understood that base (114) may also include one or more electrical contacts and/or other features operable to establish electrical communication with a complementary feature of dock (72). A shaft support structure (122) extends upwardly from base (114) and provides support to shaft assembly (160) (while still allowing shaft assembly (160) to rotate). By way of example only, shaft support structure (122) may include a bushing, bearings, and/or other features that facilitate rotation of shaft assembly (160) relative to support structure (122). As shown in FIG. 10, base (114) further includes four drive discs (120) that are rotatable relative to plate (116). Each disc (120) includes a pair of unitary pins (121) that couple with complementary recesses (not shown) in drive elements of dock (72). In some versions, one pin (121) of each pair is closer to the axis of rotation of the corresponding disc (120), to ensure proper angular orientation of disc (120) relative to the corresponding drive element of dock (72). As best seen in FIGS. 11-13, a drive shaft (124, 125, 126, 127) extends unitarily upwardly from each disc (120). As will be described in greater detail below, discs (120) are operable to provide independent rotation of shaft assembly (160), bending of articulation section (170), and translation of firing beam (190), through rotation of drive shafts (124, 125, 126, 127).

As best seen in FIG. 11, a first helical gear (130) is fixedly secured to drive shaft (124), such that rotation of the corresponding disc (120) provides rotation of first helical gear (130). First helical gear (130) meshes with a second helical gear (132), which is fixedly secured to rotary coupling (164). Thus, rotation of first helical gear (130) provides rotation of shaft assembly (160). It should be understood that rotation of first helical gear (130) about a first axis is converted into rotation of second helical gear (132) about a second axis, which is orthogonal to the first axis. A clockwise (CW) rotation of second helical gear (132) results in CW rotation of shaft assembly (160). A counter-clockwise (CCW) rotation of second helical gear (132) results in CCW rotation of shaft assembly (160). Other suitable ways in which shaft assembly (160) may be rotated will be apparent to those of ordinary skill in the art in view of the teachings herein.

As best seen in FIGS. 11-12, a spur gear (134) is fixedly secured to drive shaft (125), such that rotation of the corresponding disc (120) provides rotation of spur gear (134). Spur gear (134) meshes with a first spur pinion (136), which is fixedly secured to a pinion shaft (138). Pinion shaft (138) is supported by base (116) and rotates freely relative to base (116), such that first spur pinion (136) is rotatable as an idler. It should therefore be understood that first spur pinion (136) rotates in response to rotation of spur gear (134). First spur pinion (136) also meshes with a rack (140), which is fixedly secured to a drive block (142). Drive block (142) is secured to firing beam coupling (166). Thus, rotation of first spur pinion (136) is converted to translation of firing beam (190) via rack (140), drive block (142), and firing beam coupling (166). As noted above, firing beam (190) is operable to first close jaws (182, 184) together about tissue during a first range of distal travel of firing beam (190); then sever the tissue clamped between jaws (182, 184) during a first range of distal travel of firing beam (190). Thus tissue may be clamped and severed by rotation of drive shaft (125) via its corresponding disc (120). When this rotation is reversed, firing beam (190) retracts proximally, ultimately opening jaws (182, 184) to release tissue. Other suitable ways in which firing beam (190) may be translated will be apparent to those of ordinary skill in the art in view of the teachings herein.

With respect to articulation control, FIGS. 11-12 show a second spur pinion (144) fixedly secured to drive shaft (126), such that rotation of the corresponding disc (120) provides rotation of second spur pinion (144). Second spur pinion (144) meshes with a left rack (146), which is fixedly secured to articulation beam (174). It should be understood that articulation beam (174) will translate distally or proximally in response to rotation of drive shaft (126). Similarly, FIGS. 11 and 13 show a third spur pinion (148) fixedly secured to drive shaft (127), such that rotation of the corresponding disc (120) provides rotation of third spur pinion (148). Third spur pinion (148) meshes with a right rack (150), which is fixedly secured to articulation beam (176). It should be understood that articulation beam (176) will translate distally or proximally in response to rotation of drive shaft (127).

It should also be understood that drive shafts (126, 127) may be rotated in the same direction simultaneously in order to provide opposing translation of beams (174, 176). For instance, drive shaft (126) may be rotated clockwise to retract beam (174) proximally, with drive shaft (127) being rotated clockwise to advance beam (176) distally, to thereby deflect end effector (180) to the left (L) at articulation section (170). Conversely, drive shaft (126) may be rotated counter-clockwise to advance beam (174) distally, with drive shaft (127) being rotated counter-clockwise to retract beam (176) proximally, to deflect end effector (180) to the left (R) at articulation section (170). Other suitable ways in which end effector (180) may be articulated at articulation section (170) will be apparent to those of ordinary skill in the art in view of the teachings herein. By way of example only, articulation control may be provided in accordance with at least some of the teachings of U.S. Pub. No. 2012/0078243, now U.S. Pat. No. 9,877,720, issued Jan. 30, 2018, the disclosure of which is incorporated by reference herein; and/or U.S. Pub. No. 2013/0023868, now U.S. Pat. No. 9,545,253, issued Jan. 17, 2017, the disclosure of which is incorporated by reference herein. It should also be understood that some versions of instrument (100) may simply lack an articulation section (170) and corresponding control.

D. Exemplary Operation

In an exemplary use, arm cart (40) is used to insert end effector (180) into a patient via a trocar. Articulation section (170) is substantially straight when end effector (180) and part of shaft assembly (160) are inserted through the trocar. Drive shaft (124) may be rotated through drive features in dock (72) that are coupled with the corresponding disc (120), to position end effector (180) at a desired angular orientation relative to the tissue. Drive shafts (126, 126) may then be rotated through drive features in dock (72) that are coupled with the corresponding discs (120), to pivot or flex articulation section (170) of shaft assembly (160) in order to position end effector (180) at a desired position and orientation relative to an anatomical structure within the patient. Two layers of tissue of the anatomical structure are then captured between jaws (182, 184) by rotating drive shaft (125) to advance firing beam (190) distally through a first range of motion. Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of instrument (100) is perpendicular to the longitudinal axis defined by end effector (180), etc.). In other words, the lengths of jaws (182, 184) may be oriented perpendicular to (or at least generally transverse to) the length of the blood vessel. As noted above, flanges (192, 196) cammingly act to pivot jaw (182) toward jaw (184) when firing beam (190) is actuated distally by rotating drive shaft (125).

With tissue layers captured between jaws (182, 184) firing beam (190) continues to advance distally in response to continued rotation of drive shaft (125). As firing beam (190) continues to advance distally, distal blade (194) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (192, 196) immediately above and below jaws (182, 184), respectively, may help keep jaws (182, 184) in a closed and tightly clamping position. In particular, flanges (192, 196) may help maintain a significantly compressive force between jaws (182, 184). With severed tissue layer portions being compressed between jaws (182, 184), electrode surfaces (186, 187) are activated with bipolar RF energy by the surgeon providing a corresponding command input through controller (30) (e.g., through user input assembly (32) or footswitches (38), etc.). In some versions, electrodes (186, 187) are selectively coupled with power source (102) such that electrode surface (186, 187) of jaws (182, 184) are activated with a common first polarity while firing beam (190) is activated at a second polarity that is opposite to the first polarity. Thus, a bipolar RF current flows between firing beam (190) and electrode surfaces (186, 187) of jaws (182, 184), through the compressed regions of severed tissue layer portions. In some other versions, electrode surface (186) has one polarity while electrode surface (187) and firing beam (190) both have the other polarity. In either version (among at least some others), bipolar RF energy delivered by power source (102) ultimately thermally welds the tissue layer portions on one side of firing beam (190) together and the tissue layer portions on the other side of firing beam (190) together.

In certain circumstances, the heat generated by activated electrode surfaces (186, 187) can denature the collagen within the tissue layer portions and, in cooperation with clamping pressure provided by jaws (182, 184), the denatured collagen can form a seal within the tissue layer portions. Thus, the severed ends of the natural lumen defining anatomical structure are hemostatically sealed shut, such that the severed ends will not leak bodily fluids. In some versions, electrode surface (186, 187) may be activated with bipolar RF energy before firing beam (190) even begins to translate distally and thus before the tissue is even severed. Other suitable ways in which instrument (100) may be operable and operated will be apparent to those of ordinary skill in the art in view of the teachings herein.

Figure 14:
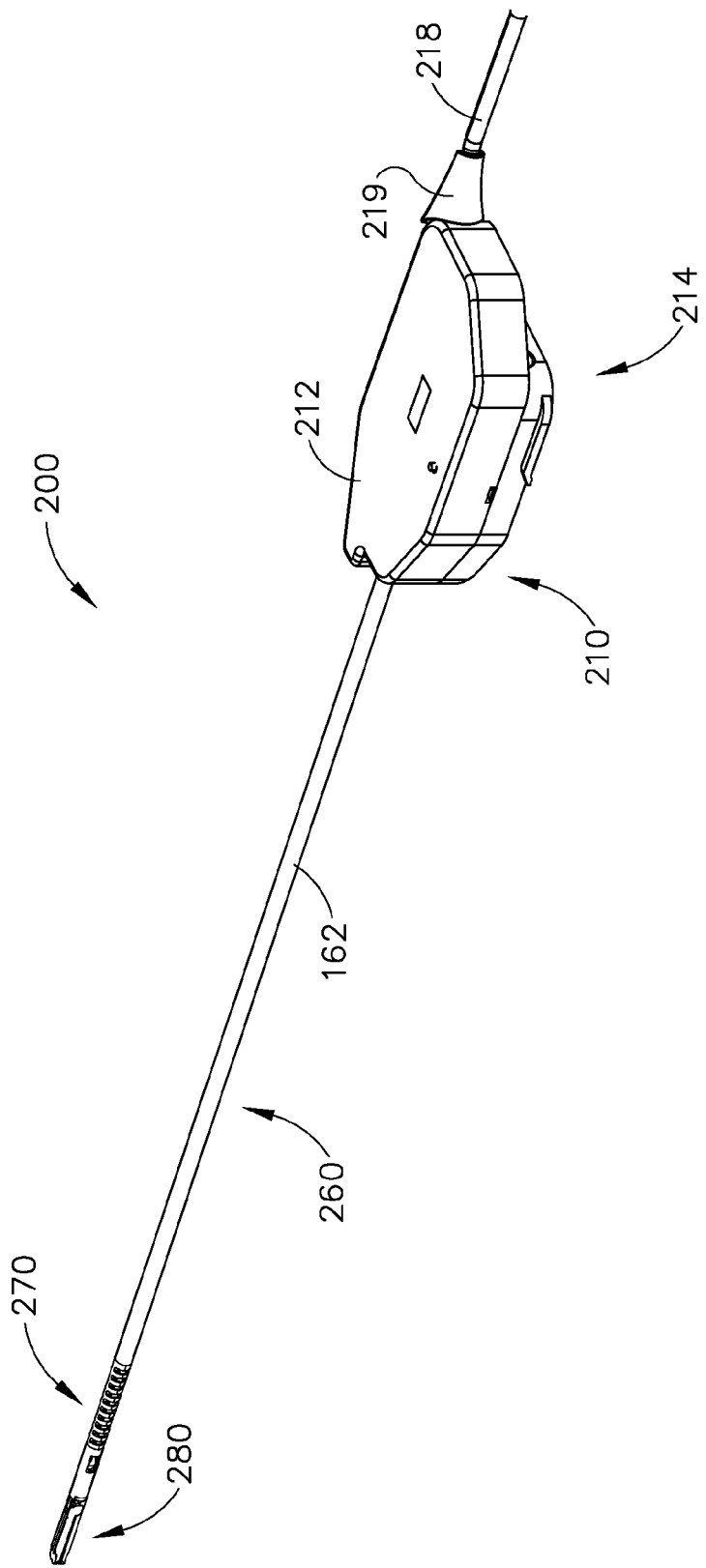
FIG. 14 depicts a perspective view of an exemplary alternative surgical instrument suitable for incorporation with the system of FIG. 1.

III. Exemplary Alternative Electrosurgical Instrument with Pulley Driven Rotation and Articulation FIG. 14 shows an exemplary alternative electrosurgical instrument (200). Instrument (200) of this example is substantially similar to instrument (100) described above in that instrument (200) has a shaft assembly (260), an articulation section (270), and an end effector (280) that are substantially identical to shaft assembly (160), articulation section (170), and end effector (180) described above. However, as discussed in more detail below, shaft assembly (260) of this example further comprises a first drive member (340) and a second drive member (342) (see FIGS. 18 and 21). Instrument (200) of this example is also operable to couple with a dock (72) of robotic arm cart (40) via an interface assembly (210). However, interface assembly (210) of this example is different from interface assembly (110) described above.

FIGS. 15-23 show interface assembly (210) of the present example in greater detail. Interface assembly (210) comprises a housing (212), a base (214), and a cable (218). Housing (212) comprises a shell that simply encloses drive components. In some versions, housing (212) also includes an electronic circuit board, chip, and/or other feature that is configured to identify instrument (200). Such identification may be carried out through cable (218). Cable (218) is configured to couple with a power source (not shown) and a controller (not shown). A strain relief (219) is provided at the interface of cable (218) and housing (212). It should be noted that housing (212) is omitted from 19-20 and 22-24 for the sake of clarity.

Figure 15:
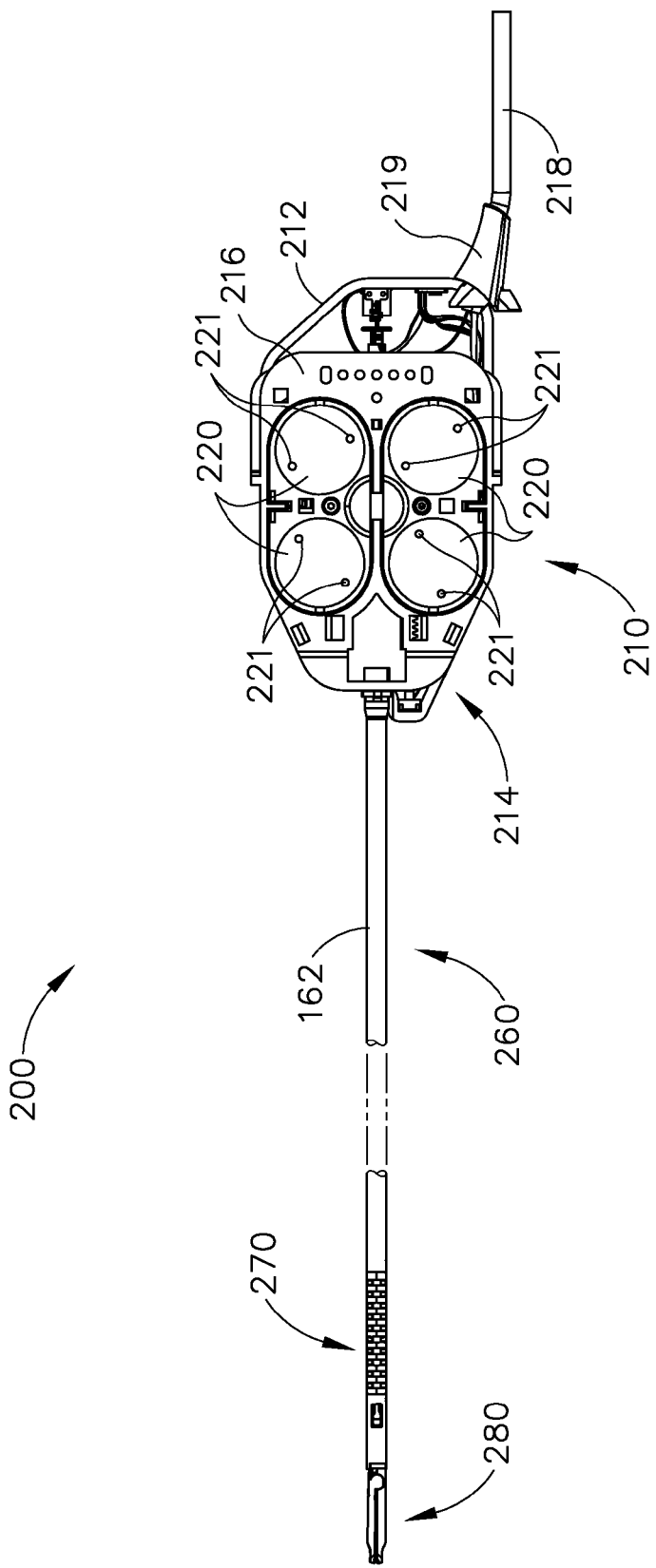
FIG. 15 depicts a bottom plan view of the surgical instrument of FIG. 14.
Figure 16:
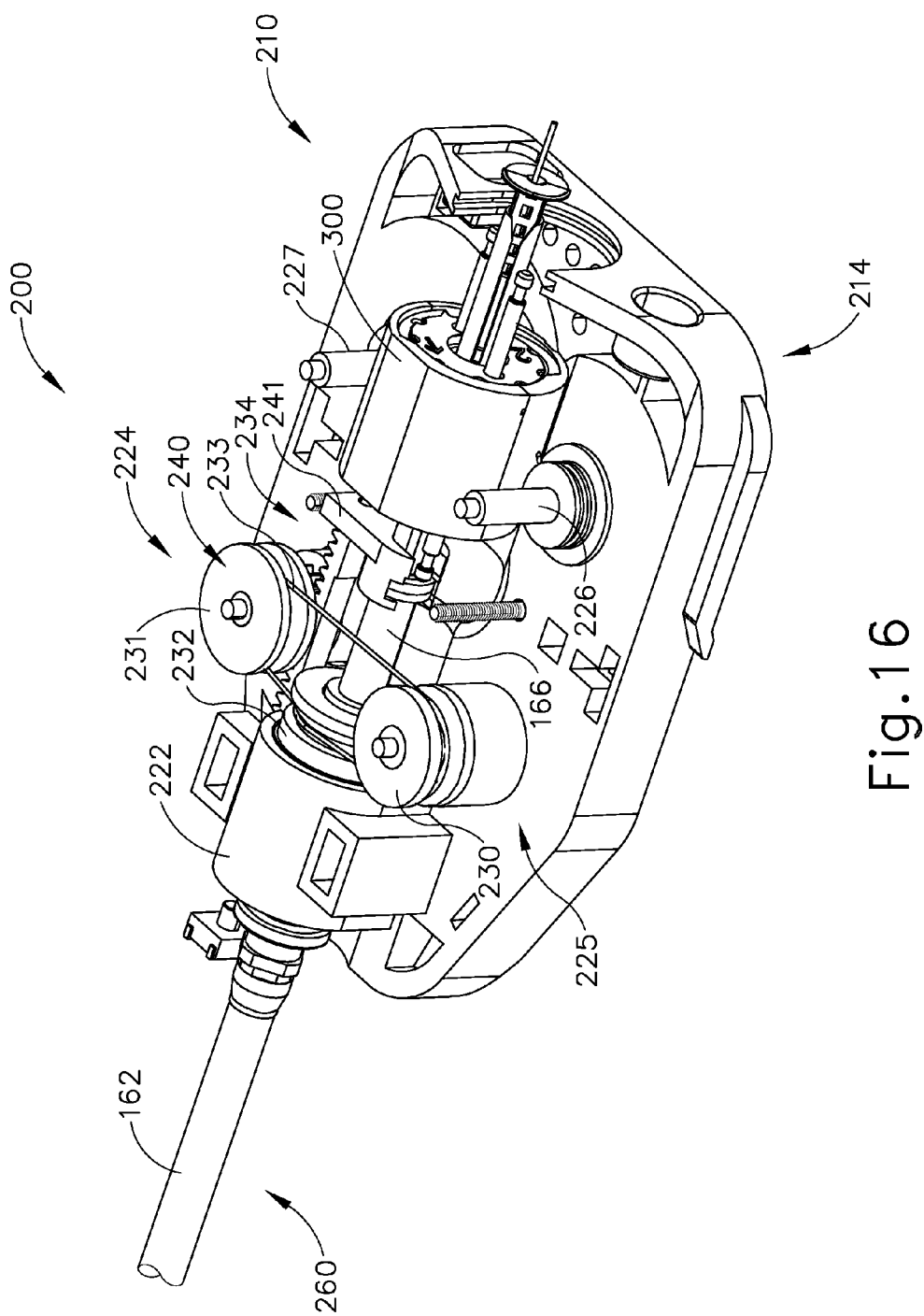
FIG. 16 depicts a perspective view of the proximal portion of the surgical instrument of FIG. 14, with a top cover removed.
Figure 17:
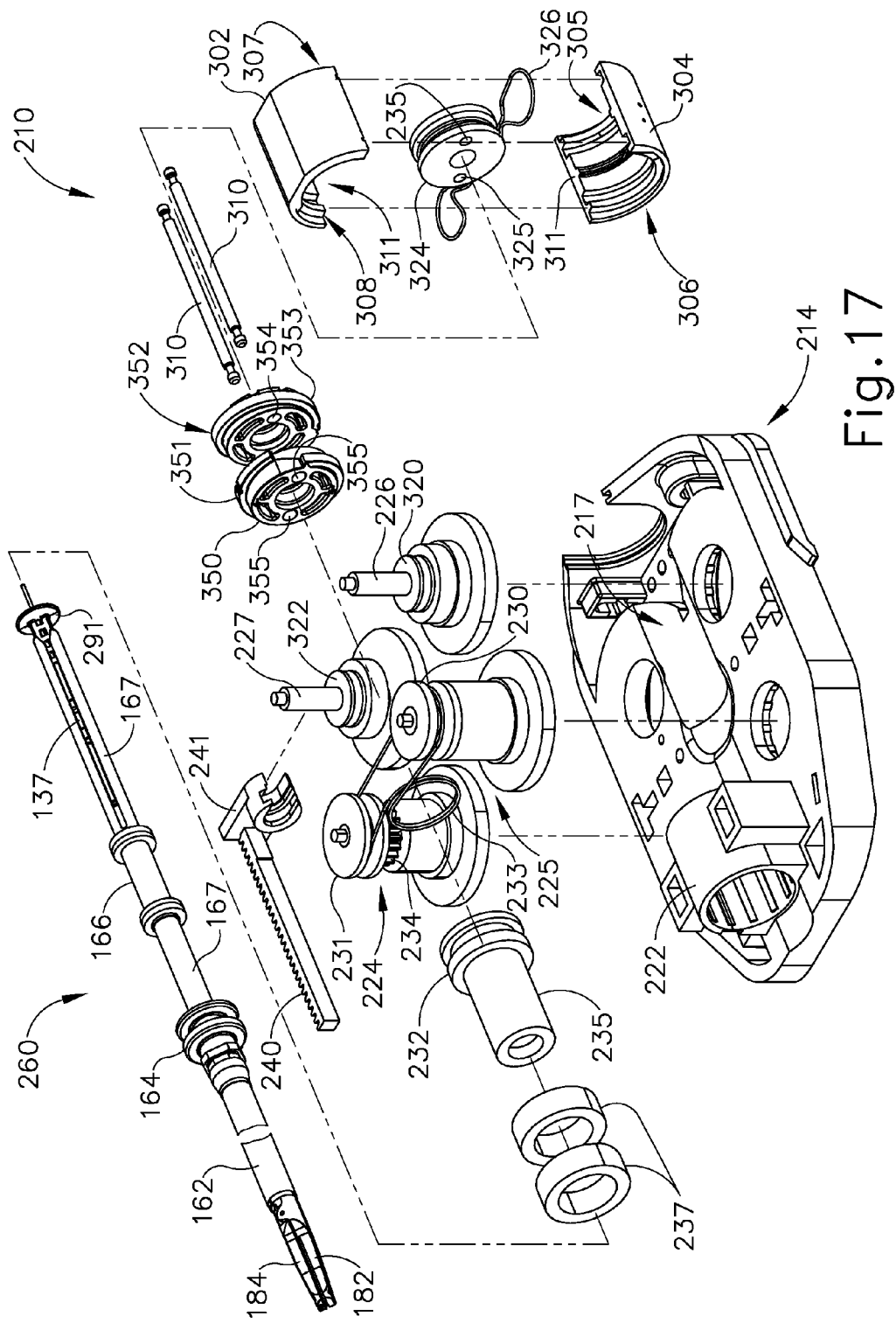
FIG. 17 depicts an exploded perspective view of the proximal portion of the surgical instrument of FIG. 14, with the top cover removed.

Base (214) includes a mounting plate (216) that engages dock (72) of robotic arm cart (40). It should be noted that plate (216) is omitted from FIGS. 19-20 and 22-24 for the sake of clarity. While not shown, it should be understood that base (214) may also include one or more electrical contacts and/or other features operable to establish electrical communication with a complementary feature of dock (72). A shaft support structure (222) extends upwardly from base (214) and provides support to shaft assembly (260) (while still allowing shaft assembly (260) to rotate). By way of example only, shaft support structure (222) may include a bushing, bearings, and/or other features that facilitate rotation of shaft assembly (260) relative to support structure (222). For instance, as shown in FIG. 17, a second pulley (232) is attached to a sleeve (235), which is fixedly secured to rotary coupling (164). Pulley (232) and sleeve (235) thus rotate unitarily with sheath (162). A pair of bushings (237) provides support for sleeve (235) and second pulley (232) while allowing second pulley (232) to rotate about the longitudinal axis defined by sheath (162). As shown in FIG. 15, base (214) further includes four drive discs (220) that are rotatable relative to plate (216). Each disc (220) includes a pair of unitary pins (221) that couple with complementary recesses (not shown) in drive elements of dock (72). In some versions, one pin (221) of each pair is closer to the axis of rotation of the corresponding disc (220), to ensure proper angular orientation of disc (220) relative to the corresponding drive element of dock (72). As best seen in FIGS. 16-17, a drive shaft (224, 225, 226, 227) extends unitarily upwardly from each disc (220). As will be described in greater detail below, discs (220) are operable to provide independent rotation of shaft assembly (260), bending of articulation section (270), and translation of firing beam (190), through rotation of drive shafts (224, 225, 226, 227).

A. Rotation of Shaft Assembly

As best seen in FIGS. 16-17, a first pulley (230) is fixedly secured to drive shaft (225), such that rotation of the corresponding disc (220) provides rotation of first pulley (230). A first idler pulley (231) is rotatably secured to drive shaft (224), such that rotation of the corresponding disc (220) does not provide rotation to first idler pulley (231). In other words, first idler pulley (231) rotates freely relative to drive shaft (224). A cable (233) is placed around first pulley (230), first idler pulley (231), and second pulley (232), which is fixedly secured to rotary coupling (164). Thus, rotation of first pulley (230) provides rotation of shaft assembly (260). It should be understood that rotation of first pulley (230) about a first axis is converted into rotation of second pulley (232) about a second axis via cable (233), with the second axis being orthogonal to the first axis. A clockwise (CW) rotation of second pulley (232) (viewed from the top) results in CW rotation of shaft assembly (260) (viewed from the proximal end). A counter-clockwise (CCW) rotation of second pulley (232) (viewed from the top) results in CCW rotation of shaft assembly (260) (viewed from the proximal end).

B. Translation of Firing Beam

As best seen in FIGS. 16-17, a spur gear (234) is fixedly secured to drive shaft (224) below idler pulley (231), such that rotation of the corresponding disc (220) provides rotation of spur gear (234). Spur gear (234) meshes with a rack (240), which is coupled at a proximal end to a clip (241). Clip (241) is coupled to firing beam coupling (166). As discussed above, translation of firing beam coupling (166) will translate firing tube (167), which will thereby translate firing beam (190). Thus, rotation of spur gear (234) is converted to translation of firing beam (190) via rack (240) and firing beam coupling (166). As noted above, firing beam (190) is operable to first close jaws (182, 184) together about tissue during a first range of distal travel of firing beam (190); then sever the tissue clamped between jaws (182, 184) during a first range of distal travel of firing beam (190). Thus tissue may be clamped and severed by rotation of drive shaft (225) via its corresponding disc (220). When this rotation is reversed, firing beam (190) retracts proximally, ultimately opening jaws (182, 184) to release tissue.

C. Bending of Articulation Section

Figure 18:
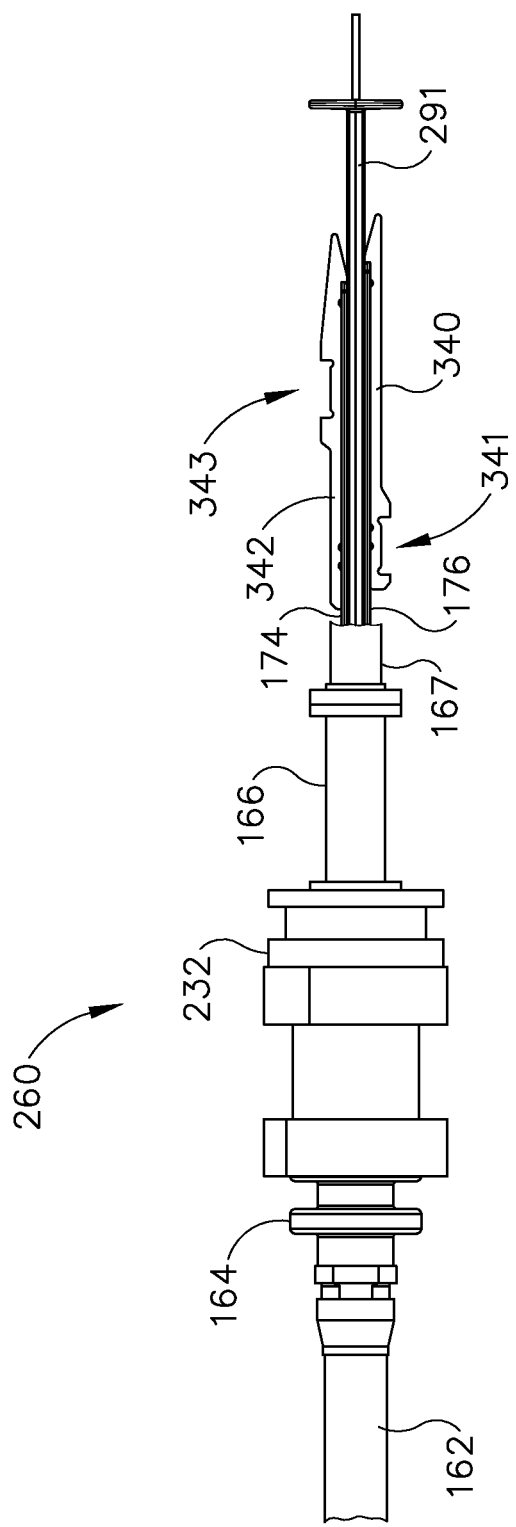
FIG. 18 depicts a detailed right side view of a shaft assembly of the surgical instrument of FIG. 14, with a proximal portion of the outer sheath omitted.

FIG. 18 shows shaft assembly (260) having a drive member (340) and a drive member (342). Drive member (340) is unitarily secured to articulation band (176) and includes a notch (341) extending laterally inwardly. Drive member (342) is unitarily secured to articulation band (174) and includes a notch (343) extending laterally inwardly. As best seen in FIG. 18, drive members (340, 342) are spaced and configured such that notches (341, 343) are at different longitudinal positions along the length of a spacer (291). As best seen in FIG. 17, a proximal portion of firing tube (167) includes longitudinally extending slots (137). Drive members (340, 342) are slidably disposed in slots (137) and notches (341,343) are radially positioned outside the outer circumference of firing tube (167). Slots (137) are configured to enable free translation of firing tube (167) relative to drive members (340, 342), to thus enable free actuation of firing beam (190) regardless of the articulation state of articulation section (270). In other words, slots (137) are configured to enable free translation of drive members (340, 342) relative to firing tube (167), to thus enable free articulation of articulation section (270) regardless of the longitudinal position of firing beam (190).

Figure 19:
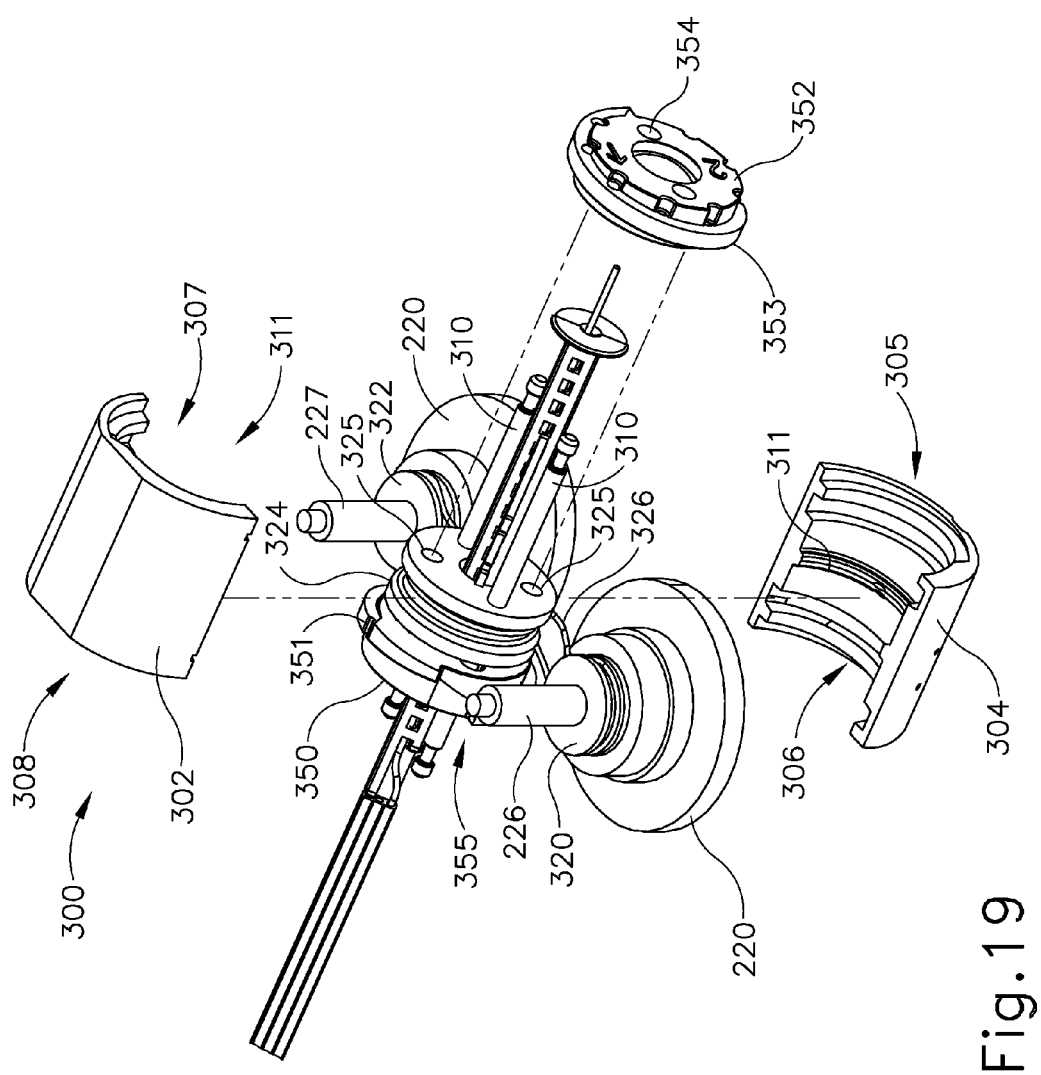
FIG. 19 depicts an exploded perspective view of articulation drive components of the surgical instrument of FIG. 14.

As shown in FIG. 19, an articulation housing (300) comprises an articulation cover (302) and an articulation base (304) configured to couple together. As best seen in FIG. 17, base (214) presents a recess (217) in which articulation housing (300) is fixedly secured. Articulation cover (302) comprises a first internal thread region (308) and a second internal thread region (307). Articulation base (304) comprises a first internal thread region (306) and a second internal thread region (305). First internal thread region (308) of articulation cover (302) and first internal thread region (306) of articulation base (304) are configured such that the threads of first internal thread region (308) and the threads of first internal thread region (306) align to form a first complete internal thread region (301) (see FIG. 21) when articulation cover (302) and articulation base (304) are coupled together. Second internal thread region (307) of articulation cover (302) and second internal thread region (305) of articulation base (304) are configured such that the threads of second internal thread region (307) of articulation cover (302) and the threads of second internal thread region (305) of articulation base (304) align to form a second complete internal thread region (309) (see FIG. 21) when articulation cover (302) and articulation base (304) are coupled together. In the present example, first internal thread region (301) and second internal thread region (309) comprise opposing threads, such that rotation in a single direction causes opposite translation within the thread regions (301, 309) (see FIGS. 22-24). For instance, first internal thread region (301) may comprise a right-handed thread pitch and second internal thread region (309) may comprise a left-handed thread pitch, or vice-versa.

Figure 20:
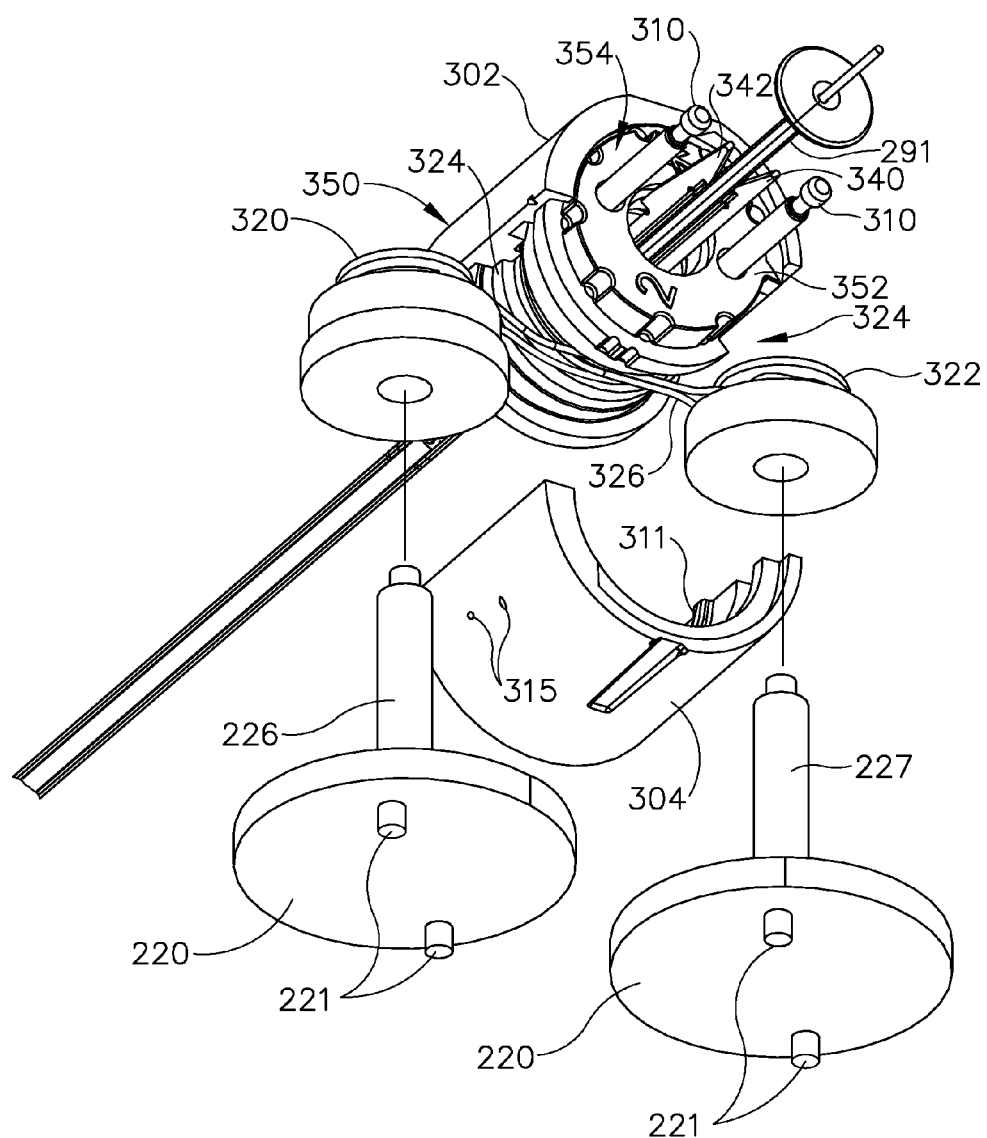
FIG. 20 depicts another exploded perspective view of the articulation drive components of FIG. 19.

It should be noted that housing (212), base (214) and particular drive components not associated with articulation are omitted from FIGS. 19-20 and 22-24 for the sake of clarity. FIGS. 19-20 show a third pulley (320) fixedly secured to drive shaft (226), such that rotation of the corresponding disc (220) provides rotation of third pulley (320). FIGS. 19-20 also show a fourth pulley (322) fixedly secured to drive shaft (226), such that rotation of the corresponding disc (220) provides rotation of fourth pulley (322). It should be understood that in some versions of surgical instrument (200), third pulley (320) or fourth pulley (322) may simply freewheel, thereby acting as an idler pulley. In such versions, the idler pulley may rotate freely relative to its drive shaft; or the idler pulley's drive shaft may rotate freely relative to an associated drive element of dock (72). For instance, the drive disc associated with the idler pulley mar simply lack unitary pins (221). A cable (326) is placed around third pulley (320), fourth pulley (322), and a fifth pulley (324), which is rotatably secured within an articulation housing (300) such that fifth pulley (324) is free to rotate within housing articulation (300). Thus, rotation of third pulley (320) and fourth pulley (322) provides rotation of fifth pulley (324). As best seen in FIG. 20, cable (326) would be routed through openings (315) in articulation base (304). An annular protrusion (311) within articulation housing (300) prevents translation of fifth pulley (324) along the longitudinal axis defined by sheath (162). It should be understood that rotation of third pulley (320) and fourth pulley (322) about a first and second axes is converted into rotation of fifth pulley (324) about a third axis, which is orthogonal to the first and second axes. A CW rotation of third pulley (320) (viewed from the top) and fourth pulley (322) (viewed from the top) results in CCW rotation of fifth pulley (324) (viewed from the proximal end). A CCW rotation of third pulley (320) (viewed from the top) and fourth pulley (322) (viewed from the top) results in CW rotation of fifth pulley (324) (viewed from the proximal end).

As best seen in FIG. 19, two pins (310) are disposed within bores (325) of fifth pulley (324). Firing tube (167) is disposed within a central bore (325) of fifth pulley (324). The internal diameter of central bore (325) is configured to allow firing tube (167) to freely translate and rotate irrespective of the rotation of fifth pulley (324). Thus, rotation of fifth pulley (324) will have no effect upon firing tube (167), and translation or rotation of firing tube (167) will have no effect upon fifth pulley (324).

FIG. 19 shows a first lead screw (350) and a second lead screw (352). First lead screw (350) presents a first external thread (351). First lead screw (350) is configured to matingly thread into first internal thread region (301) of articulation housing (300). Second lead screw (352) presents a second external thread (353). Second lead screw (352) is configured to matingly thread into second internal thread region (309) of articulation housing (300). In the present example, first lead screw (350) and second lead screw (352) comprise opposing threads, such that rotation in a single direction causes opposite translation within the thread regions (301, 309). For instance, first lead screw (350) may comprise a right-handed thread pitch and second lead screw (352) may comprise a left-handed thread pitch, or vice-versa. Pins (310) are disposed within bores (355) of first lead screw (350) and bores (354) of second lead screw (352). Thus, as fifth pulley (324) rotates, pins (310) cause first lead screw (350) and second lead screw (352) to rotate in the same direction. As noted above, first internal thread region (301) and second internal thread region (309) comprise opposing threads, such that rotation in a single direction causes opposite translation within the thread regions (301,309). Thus rotation of first lead screw (350) and second lead screw (352) will cause opposing translation of first lead screw (350) within first internal thread region (301) of articulation housing (300) and second lead screw (352) within second internal thread region (309) of articulation housing (300). For instance, CW rotation of fifth pulley (324) (viewed from the proximal end) may cause first lead screw (350) to move proximally toward fifth pulley (324) and second lead screw (352) to simultaneously move distally toward fifth pulley (324) along the longitudinal axis defined by sheath (162); and/or CCW rotation of fifth pulley (324) may cause first lead screw (350) to move distally from fifth pulley (324) and second lead screw (352) to simultaneously move proximally from fifth pulley (324) along the longitudinal axis defined by sheath (162). Thus, it should be understood that rotation of third pulley (320) and fourth pulley (322) provides rotation of fifth pulley (324) which in turn causes rotation and opposing translation of first lead screw (350) and second lead screw (352) along the longitudinal axis defined by sheath (162).

Figure 21:
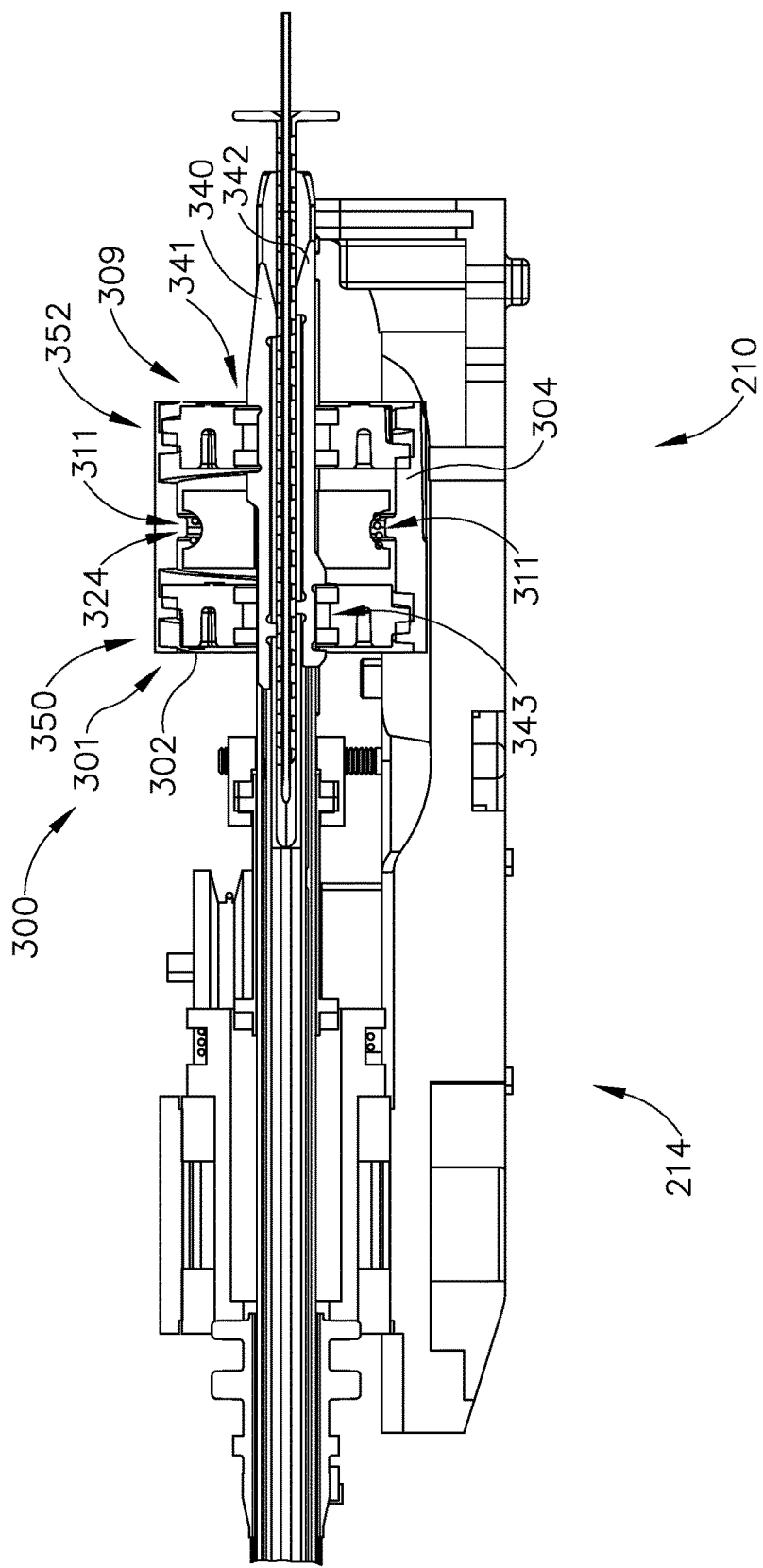
FIG. 21 depicts a detailed cross-sectional view of the proximal portion of the surgical instrument of FIG. 14, with the top cover removed.
Figure 22:
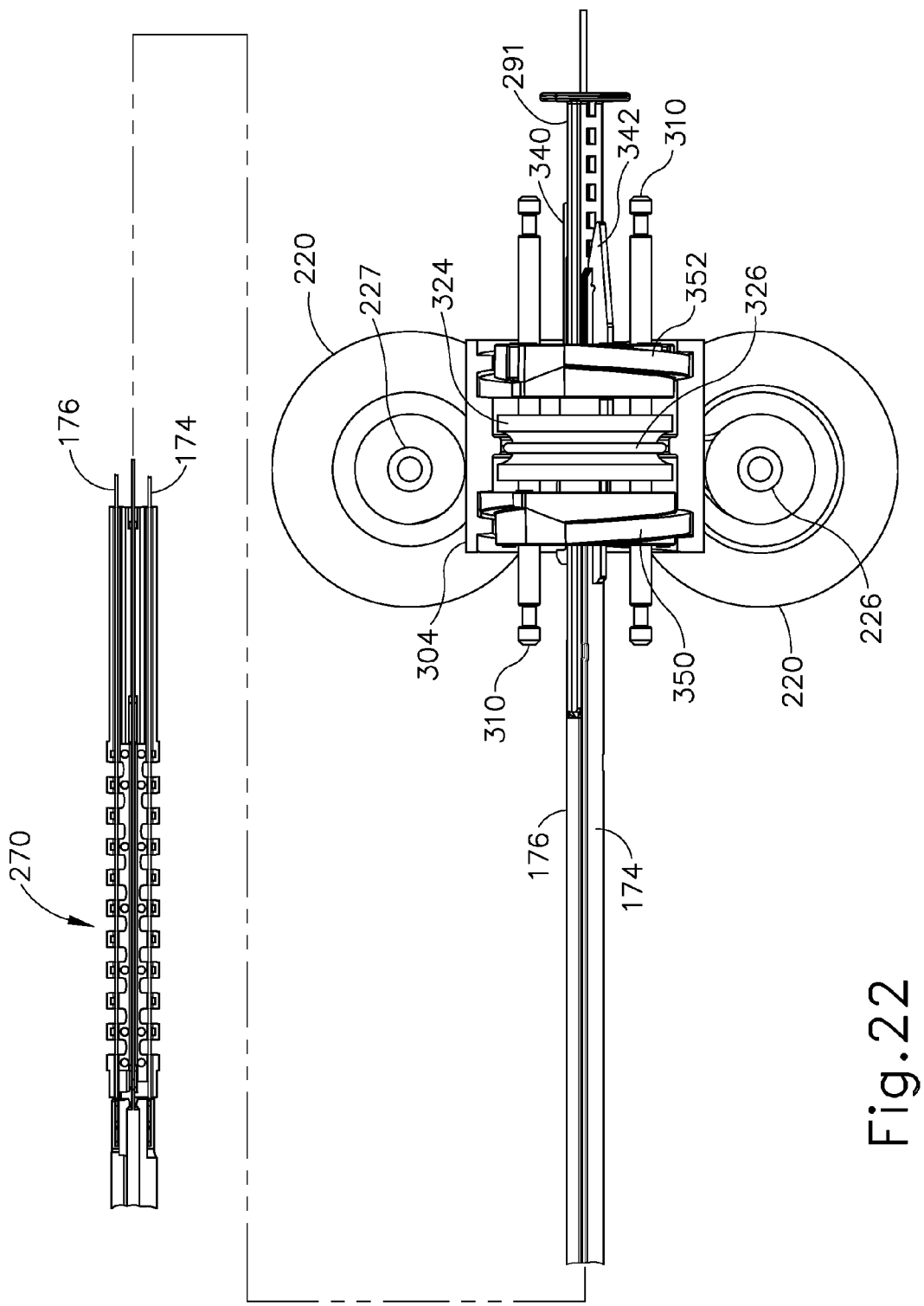
FIG. 22 depicts a top plan view of the articulation drive components of the surgical instrument of FIG. 14 with an articulation section of the surgical instrument of FIG. 14 in a first position.
Figure 23:
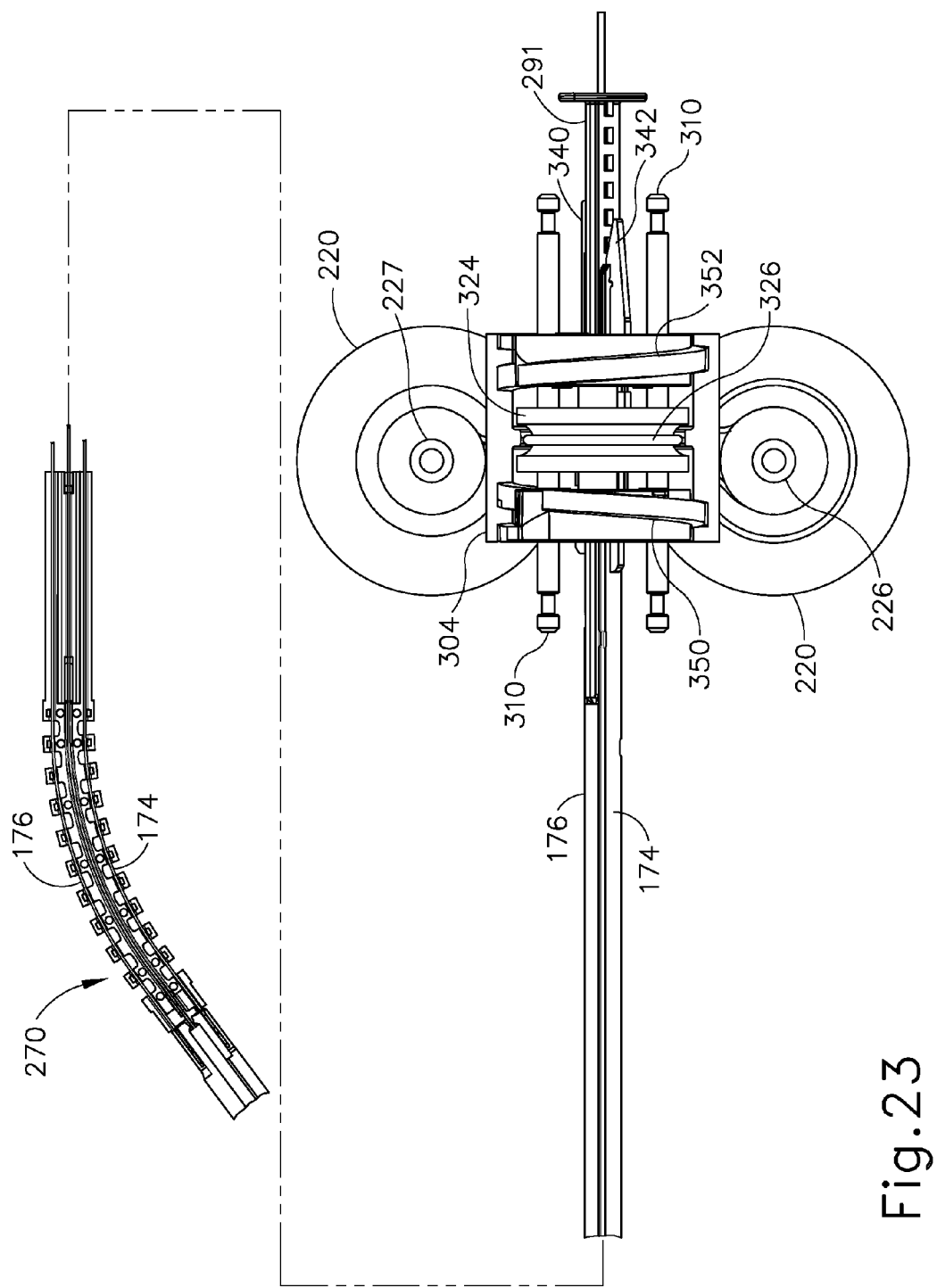
FIG. 23 depicts a top plan view of the articulation drive components of the surgical instrument of FIG. 14 with the articulation section of the surgical instrument of FIG. 14 in a second position.
Figure 24:
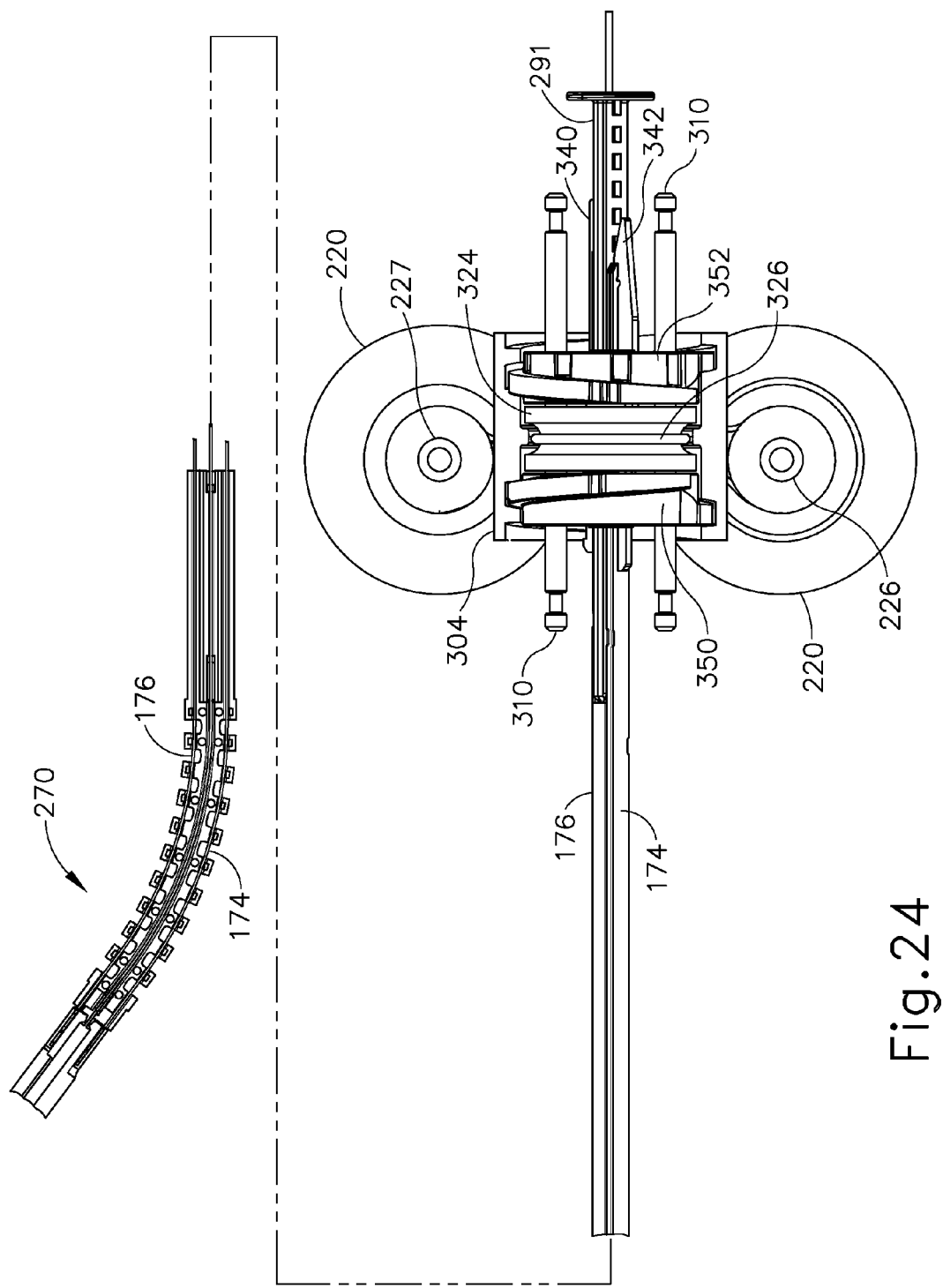
FIG. 24 depicts a top plan view of the articulation drive components of the surgical instrument of FIG. 14 with the articulation section of the surgical instrument of FIG. 14 in a third position.

As best seen in FIG. 21, first lead screw (350) is disposed within notch (341) of drive member (340), and second lead screw (352) is disposed within notch (343) of drive member (342). Thus, as first lead screw (350) and second lead screw (352) translate along the longitudinal axis defined by sheath (162), drive members (340, 342) will correspondingly translate. Therefore, it should be understood that articulation bands (174,176) will translate distally or proximally in response to rotation of drive shafts (226,227) thus causing articulation of articulation section (270). For instance, as shown in FIG. 23, CW rotation of fifth pulley (324) may cause first lead screw (350), and consequentially drive member (340), to move proximally toward fifth pulley (324) and second lead screw (352), and consequentially drive member (342), to simultaneously move distally toward fifth pulley (324) along the longitudinal axis defined by sheath (162) Such movement will cause articulation band (174) and articulation band (176) to move in opposing directions, thus causing articulation of articulation section (270) in a first direction. On the other hand, as shown in FIG. 24, CCW rotation of fifth pulley (324) may cause first lead screw (350), and consequentially drive member (340), to move distally from fifth pulley (324) and second lead screw (352), and consequentially drive member (342), to simultaneously move proximally from fifth pulley (324) along the longitudinal axis defined by sheath (162). Such movement will cause articulation band (174) and articulation band (176) to move in opposing directions, thus causing articulation of articulation section (270) in a second direction. It should be noted that first lead screw (350) and second lead screw (352) rotate freely relative to drive members (340, 342) even though drive members (340, 342) translate with first lead screw (350) and second lead screw (352).

It should be understood that some versions of instrument (200) may simply lack an articulation section (170) and corresponding control. It should also be understood that in some versions, one or both of third pulley (320) and/or fourth pulley (322) may provide rotation to articulation housing (300) instead of fifth pulley (324). In such versions, first lead screw (350), second lead screw (352), and pins (310) would not rotate within articulation housing (300); but lead screws (350, 352) would translate within articulation housing (300) as articulation housing (300) is rotated by one or both of third pulley (320) and/or fourth pulley (322).

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc.

In versions where the teachings herein are applied to a surgical stapling instrument, it should be understood that the teachings herein may be combined with the teachings of one or more of the following, the disclosures of all of which are incorporated by reference herein: U.S. Pat. No. 7,380,696; U.S. Pat. No. 7,404,508; U.S. Pat. No. 7,455,208; U.S. Pat. No. 7,506,790; U.S. Pat. No. 7,549,564; U.S. Pat. No. 7,559,450; U.S. Pat. No. 7,654,431; U.S. Pat. No. 7,780,054; U.S. Pat. No. 7,784,662; and/or U.S. Pat. No. 7,798,386. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus for operating on tissue, the apparatus comprising:
   (a) an end effector;
      (i) a first jaw, and
      (ii) a second jaw, wherein the first jaw is movable toward the second jaw to clamp tissue between the first and second jaw;
   (b) an elongate shaft, wherein the elongate shaft defines a longitudinal axis, wherein the elongate shaft comprises:
      (i) a distal end, wherein the end effector is positioned at the distal end of the elongate shaft,
      (ii) a proximal end,
      (iii) an articulation section, wherein the articulation section is operable to deflect at least part of the end effector away from the longitudinal axis, and
      (iv) a first pulley, wherein the first pulley is rotatable about the longitudinal axis of the elongate shaft; and (c) an interface assembly associated with the proximal end of the elongate shaft, wherein the interface assembly comprises:
  (i) a plurality of drive discs, wherein each of the drive discs of the plurality of drive discs is associated with a respective drive shaft,
  (ii) a second pulley, wherein the second pulley is fixedly secured to a first drive shaft,
  (iii) a third pulley, wherein the third pulley is rotatably secured with a second drive shaft such that the third pulley is configured to rotate freely relative to the second drive shaft, and
  (iv) a cable coupling the first pulley with the second pulley and with the third pulley, wherein each of the first, second, and third pulleys are coupled with the cable such that the first pulley, the second pulley, and the third pulley are operable to drive articulation of the elongate shaft or rotation of one or both of the elongate shaft or the end effector about the longitudinal axis of the elongate shaft
  wherein the first pulley is positioned between the second and third pulleys within the interface assembly,
  wherein the second drive shaft is operatively connected to the end effector and configured to be selectively rotatably driven to move the first jaw toward the second jaw for clamping tissue therebetween independent of rotation of the third pulley rotatably secured thereon.

2. The apparatus of claim 1, wherein the interface assembly further comprises:
  (i) a housing, wherein the housing comprises:
    (A) a first internal thread region,
    (B) a second internal thread region, wherein the first internal thread region and the second internal thread region comprise threads having different thread directions, and
    (C) an intermediate region, wherein the intermediate region separates the first internal thread region and the second internal thread region, and wherein the first pulley is rotatably disposed within the intermediate region of the housing,
  (ii) a first threaded member, wherein the first threaded member is configured to matingly thread into the first internal thread region of the housing, and
  (iii) a second threaded member, wherein the second threaded member is configured to matingly thread into the second internal thread region of the housing, and wherein the first threaded member and the second threaded member are operable to drive articulation of the end effector.

3. The apparatus of claim 2, wherein the interface assembly further comprises a plurality of pins, wherein the first pulley, the first threaded member, and the second threaded member each comprise a plurality of bores, wherein the pins are disposed within the bores of the first pulley, the first threaded member, and the second threaded member such that each pin is disposed within the first pulley, the first threaded member, and the second threaded member, and wherein the pins are configured to cause the first pulley, the first threaded member, and the second threaded member to rotate together.

4. The apparatus of claim 3, wherein the first threaded member and the second threaded member are configured to translate in opposite directions along the longitudinal axis of the elongate shaft in response to concurrent rotation of the first pulley, the first threaded member, and the second threaded member.

5. The apparatus of claim 4, wherein the shaft assembly further comprises:
  (i) a first articulation band, wherein the first articulation band is coupled to a first drive member, and wherein the first drive member is configured to translate along an axis parallel to the longitudinal axis of the elongate shaft in response to translation of the first threaded member, and
  (ii) a second articulation band, wherein the second articulation band is coupled to a second drive member, and wherein the second drive member is configured to translate along an axis parallel to the longitudinal axis of the elongate shaft in response to translation of the second threaded member.

6. The apparatus of claim 5, wherein the first drive member comprises a first notch, wherein the first threaded member is disposed within the first notch, wherein the second drive member comprises a second notch, and wherein the second threaded member is disposed within the second notch.

7. The apparatus of claim 6, wherein the interface assembly further comprises:
  (i) a spur gear fixedly secured to the second drive shaft such that the third pulley, the spur gear, and the second drive shaft are coaxially aligned, and
  (ii) a rack, wherein the spur gear meshes with the rack, and wherein the rack is operable to drive the first jaw toward the second jaw.

8. The apparatus of claim 1, wherein the second drive shaft and the third pulley are coaxially aligned.

9. The apparatus of claim 8, wherein the interface assembly further comprises:
  (i) a spur gear fixedly secured to the second drive shaft such that the third pulley, the spur gear, and the second drive shaft are coaxially aligned, and
  (ii) a rack, wherein the spur gear meshes with the rack, and wherein the rack is operable to drive the first jaw toward the second jaw.

10. The apparatus of claim 9, wherein at least one of the jaws comprises at least one electrode, wherein the at least one electrode is operable to deliver RF energy to tissue clamped between the first and second jaw.

11. The apparatus of claim 1, wherein the first pulley is fixedly secured to the elongate shaft, wherein the first pulley, the second pulley, and the third pulley are operable to drive rotation of one or both of the elongate shaft or the end effector about the longitudinal axis of the elongate shaft, and wherein the third pulley is an idler pulley.

12. The apparatus of claim 11, wherein the interface assembly further comprises:
  (i) a fourth pulley, wherein the fourth pulley is fixedly secured to a third drive shaft,
  (ii) a fifth pulley, wherein the fifth pulley is rotatably secured within a housing, and wherein the fifth pulley is rotatable about the longitudinal axis of the elongate shaft,
  (iii) a sixth pulley, wherein the sixth pulley is associated with a fourth drive shaft, and
  (iv) a cable disposed about the fourth pulley, the fifth pulley, and the sixth pulley, and wherein the fourth pulley, the fifth pulley, and the sixth pulley are operable to drive articulation of the articulation section.

13. The apparatus of claim 12, wherein the sixth pulley is fixedly secured to the fourth drive shaft.

14. An apparatus for operating on tissue, the apparatus comprising:
(a) an end effector;
 (i) a first jaw, and
 (ii) a second jaw, wherein the first jaw is movable toward the second jaw to clamp tissue between the first and second jaw;
(b) an elongate shaft, wherein the elongate shaft defines a longitudinal axis, wherein the elongate shaft comprises:
 (i) a distal end, wherein the end effector is positioned at the distal end of the elongate shaft,
 (ii) a proximal end, and
 (iii) a first pulley, wherein the first pulley is fixedly secured to the elongate shaft; and
(c) an interface assembly associated with the proximal end of the elongate shaft, wherein the interface assembly comprises:
 (i) a plurality of drive discs, wherein each of the drive discs of the plurality of drive discs is associated with a respective drive shaft,
 (ii) a second pulley, wherein the second pulley is fixedly secured to a first drive shaft,
 (iii) a third pulley, wherein the third pulley is rotatably secured with a second drive shaft such that the third pulley is configured to rotate freely relative to the second drive shaft, and
 (iv) a cable coupling the first pulley with the second pulley and with the third pulley, wherein each of the first, second, and third pulleys are coupled with the cable such that the first pulley, the second pulley, and the third pulley are operable to drive rotation of one or both of the elongate shaft or the end effector about the longitudinal axis of the elongate shaft
 wherein the first pulley is positioned between the second pulley and the third pulley within the interface assembly
 wherein the second drive shaft is operatively connected to the end effector and configured to be selectively rotatably driven to move the first jaw toward the second jaw for clamping tissue therebetween independent of rotation of the third pulley rotatably secured thereon.

15. The apparatus of claim 14, wherein
at least one of the jaws comprises at least one electrode, wherein the at least one electrode is operable to deliver RF energy to tissue clamped between the first and second jaw.

16. The apparatus of claim 15, wherein the interface assembly further comprises:
(i) a spur gear fixedly secured to the second drive shaft, and
(ii) a rack, wherein the spur gear meshes with the rack, and wherein the rack is operable to drive movement of the first jaw toward the second jaw.

17. An apparatus for operating on tissue, the apparatus comprising:
(a) an end effector;
 (i) a first jaw, and
 (ii) a second jaw, wherein the first jaw is movable toward the second jaw to clamp tissue between the first and second jaw;
(b) an elongate shaft, wherein the elongate shaft defines a longitudinal axis, wherein the elongate shaft comprises:
 (i) a distal end, wherein the end effector is positioned at the distal end of the elongate shaft,
 (ii) a proximal end, and
 (iii) an articulation section, wherein the articulation section is operable to deflect at least part of the end effector away from the longitudinal axis;
(c) an interface assembly associated with the proximal end of the elongate shaft, wherein the interface assembly comprises:
 (i) a plurality of drive discs, wherein each of the drive discs of the plurality of drive discs is associated with a respective drive shaft,
 (ii) a first pulley, wherein the first pulley is fixedly secured to a first drive shaft,
 (iii) a second pulley, wherein the second pulley is rotatably secured with a second drive shaft such that the second pulley is configured to rotate freely relative to the second drive shaft,
 (iv) a third pulley,
 (v) a cable coupling the first pulley with the second pulley and with the third pulley, wherein each of the first, second and third pulleys are coupled with the cable, wherein the second drive shaft is operatively connected to the end effector and configured to be selectively rotatably driven to move the first jaw toward the second jaw for clamping tissue therebetween independent of rotation of the second pulley rotatably secured thereon,
 (vi) a housing, wherein the housing comprises a first internal thread region, a second internal thread region, and an intermediate region, wherein the first internal thread region and the second internal thread region comprise threads having different thread directions, wherein the intermediate region separates the first internal thread region from the second internal thread region, and wherein the third pulley is rotatably disposed within the intermediate region of the housing;
 (vii) a first threaded member, wherein the first threaded member is configured to matingly thread into the first internal thread region of the housing; and
 (viii) a second threaded member, wherein the second threaded member is configured to matingly thread into the second internal thread region of the housing, wherein the first threaded member and the second threaded member are configured to rotate together with the third pulley, and wherein the first threaded member and the second threaded member are operable to drive articulation of the end effector.

18. The apparatus of claim 17, wherein the elongate shaft further comprises:
(i) a first articulation band, wherein the first articulation band is coupled to the first drive member, and wherein the first drive member is configured to translate along the longitudinal axis of the elongate shaft in response to translation of the first threaded member, and
(ii) a second articulation band, wherein the second articulation band is coupled to a second drive member, and wherein the second drive member is configured to translate along the longitudinal axis of the elongate shaft in response to translation of the second threaded member.

* * * * *